(12) United States Patent
Nakami et al.

(10) Patent No.: US 7,783,430 B2
(45) Date of Patent: Aug. 24, 2010

(54) GENOTYPING RESULT EVALUATION METHOD AND SYSTEM

(75) Inventors: Yu Nakami, Tokyo (JP); Ryo Nakashige, Tokyo (JP); Yasuyuki Nozaki, Tokyo (JP); Toshiko Matsumoto, Tokyo (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 578 days.

(21) Appl. No.: 11/705,055

(22) Filed: Feb. 12, 2007

(65) Prior Publication Data

US 2007/0202526 A1 Aug. 30, 2007

(30) Foreign Application Priority Data

Feb. 28, 2006 (JP) .............................. 2006-051846

(51) Int. Cl.
*G06F 7/00* (2006.01)

(52) U.S. Cl. ............................. 702/19; 702/20; 703/11; 703/12; 703/13; 707/102; 435/6; 536/23.1; 536/24.5

(58) Field of Classification Search ........................ None
See application file for complete search history.

(56) References Cited

U.S. PATENT DOCUMENTS

| | | | | |
|---|---|---|---|---|
| 2002/0116135 | A1* | 8/2002 | Pasika et al. | ................... 702/21 |
| 2006/0052946 | A1* | 3/2006 | Yukawa et al. | ................ 702/20 |
| 2006/0122791 | A1* | 6/2006 | Matsumoto et al. | ........... 702/20 |
| 2007/0134706 | A1* | 6/2007 | Matsumoto et al. | ............ 435/6 |

OTHER PUBLICATIONS

Holt, Cydne L., Buoncristiani, Martin, Wallin, Jeanette M., Nguyen, Theresa, Lazaruk, Katherine D., and Walsh, P.S., "TWGDAM Validation of AmpFlSTR™ PCR Amplification Kits for Forensic DNA Casework", J Forensic Sci. 2002; 47(1): 66-96.

Wallin, Jeanette M., Buoncristiani, Martin R., Lazaruk, Katherine D., Fildes, Nicola, Holt, Cydne L., and Walsh, P. Sean, "TWGDAM Validation of the AMPFlSTR™ Blue PCR Amplification Kit for Forensic Casework Analysis", J. Forensic Sci. 1998; 43(4):854-870.

Leclair, Benoît, Frégeau, Chantal J., Bowen, Kathy L., and Fourney, Ron M., "Systematic Analysis of Stutter Percentages and Allele Peak Height and Peak Area Ratios at Heterozygous STR Loci for Forensic Casework and Database Samples", J Forensic Sci., 2004, 49(5):967-980.

Smith, Jeffrey R., Cartpen, John D., Brownstein, Michael J., Ghosh, Soumitra, Magnuson, Victoria L., Gilbert, Dennis A., Trent, Jeffrey M., and Collins, Francis S., "Approach to Genotyping Errors Caused by Nontemplated Nucleotide Addition by *Taq* DNA Polymerase", Genome Research, 1995, 5:312-317.

Johansson, Asa, Karlsson, Patrik, and Gyllensten, Ulf, "A Novel Method for Automatic Genotyping of Microsatellite Markers Based no Parametric Pattern Recognition", Hum Genet, 2003, 113:316-324.

* cited by examiner

*Primary Examiner*—Mary K Zeman
(74) *Attorney, Agent, or Firm*—Stites & Harbison, PLLC; Juan Carlos A. Marquez, Esq

(57) ABSTRACT

A method and a system for evaluating results of differentiating genotype signals and noise signals when a DNA fragment containing a gene to be analyzed is amplified by PCR and detected by electrophoresis are provided.

An outlier of genotyping results is detected based on the fact that, when using the same marker, the height ratio of a stutter peak to a true peak and the height ratio of a +A peak to a true peak are reproducible, and that a constant size value is obtained with the use of the same allele of the same marker. In addition, a waveform obtained in past processes with the use of the same marker or the same allele is obtained utilizing a database by focusing on reproducibility. Also, a database is extended so as to obtain improved evaluation ability in a manner such that appropriate waveform data from which an outlier is not obtained is additionally registered in a database.

4 Claims, 19 Drawing Sheets

FIG. 18

Individual A
...GCT|ATATAT|CTGAGTAAT...
...GCT|ATATATAT|CTGAG...

Individual B
...GCT|ATATATATATAT|CTG...
...GCT|ATATAT|CTGAGTAAT...

Individual C
...GCT|ATATATAT|CTGAGTA...
...GCT|ATATATAT|CTGAGTA...

GENOTYPING RESULT EVALUATION METHOD AND SYSTEM

BACKGROUND OF THE INVENTION

1. Field of the Invention

The present invention relates to a method and a system for evaluating genotyping results for analytic work of determining genotypes that are believed to be involved in differences among individual organisms (e.g., differences in terms of appearance and susceptibility to diseases). In particular, the present invention relates to a method and a system for evaluating results of distinguishing genotype signals from noise signals generated by amplifying DNA fragments that contain genes to be analyzed by PCR and detecting them by electrophoresis.

2. Background Art

Sequence determination of whole genomes of a variety of organisms such as humans has been completed. In the cases of organisms such as humans that have been decoded, genetic analysis studies have been actively conducted with regard to whole genomes and relatively large regions of such genomes. In particular, in medical studies, techniques for automatically determining many genotypes have been gaining attention for the purpose of identifying genes related to the presence or absence of diseases and the presence or absence of favorable effects or adverse effects of medicines, for example. In addition, in order to improve determination accuracy, a technique for evaluating automatically determined individual genotypes has been awaited.

Microsatellites

In general, many portions genomes of individual organisms belonging to the same species have completely identical nucleotide sequences. However, it has been known that some portions of genomes have nucleotide sequences that differ among different individuals. Such differences found in nucleotide sequences of individual genomes are referred to as polymorphisms. Several different types of polymorphisms are known to exist. In particular, the use of SNPs (single nucleotide polymorphisms) and microsatellites for analysis studies has been gaining attention.

The term "microsatellite" indicates a sequence in which several to several tens of repetitions of a short sequence pattern of 2 to 6 nucleotides appear. Human genomes contain more than several tens of thousands of microsatellites. FIG. 18 shows examples of microsatellites that appear in genomes. A set of nucleotides repeated in a microsatellite is referred to as a "unit." The number of nucleotides contained in such a unit is referred to as a "unit length." For instance, in the case of a microsatellite having a pattern "ATATATAT . . . " as shown in FIG. 18, the unit consists of "AT" and the unit length is 2 nucleotides. As shown in FIG. 18, there are differences among microsatellites (polymorphisms) having the same unit and the same unit length in terms of the number of units that are repeated.

As described above, since SNPs and microsatellites are associated with polymorphisms, they are easily distinguishable from other nucleotide sequences in genomes and they are experimentally detectable with ease. In the cases of some biological species, approximate positions of SNPs and microsatellites in genomes have been known. Thus, SNPs and microsatellites can be used as positional indicators in genomes. For these characteristics, SNPs and microsatellites are referred to as DNA markers. In particular, microsatellites contain a plurality of nucleotides so as to have greater information content compared with SNPs. Thus, microsatellites have often been used as DNA markers in genome-wide analysis studies.

As shown in FIG. 18, individuals of many organisms have the diploid genome (homologous chromosomes) derived from a female gamete and a male gamete. Genes that exist on corresponding sites in the diploid genome are called alleles. Such a combination of alleles is referred to as a genotype. As described above, SNPs and microsatellites in genomes are portions having nucleotide sequences that differ among different individuals. In general, two or three alleles are found in SNPs, while on the other hand, several to 20 types of alleles or more are found in microsatellites.

In an example shown in FIG. 18, individual A has an allele in which a unit "AT" is repeated 3 times and an allele in which the same unit is repeated 5 times, while on the other hand, individual B has an allele in which a unit "AT" is repeated 6 times and an allele in which the same unit is repeated 3 times. Also, individual C has 2 alleles each in which a unit "AT" is repeated 4 times. The state in which individuals have two different alleles (e.g., individuals A and B) is referred to as heterozygosity. Meanwhile, the state in which individuals have the two of the same allele (e.g., individual C) is referred to as homozygosity.

PCR and Electrophoresis Experimentation

With the use of microsatellites as DNA markers, microsatellite portions in a genome are extracted and detected by an experiment involving PCR (polymerase chain reaction), electrophoresis, and the like. PCR is an experimental technique whereby a sample can be obtained at a certain yield by allowing a pair of nucleotide sequences at both ends of a microsatellite, which are called primer sequences, to be subjected to a reaction with a DNA replicase so as to repeatedly replicate and amplify DNA fragments each comprising a microsatellite sandwiched by a pair of primer sequences. Electrophoresis, including gel electrophoresis and capillary electrophoresis, is an experimental technique whereby amplified DNA fragments are allowed to migrate in a charged migration path such that DNA fragments having different lengths are separated depending on different migration rates, based on molecular weights, charged levels, and the like. FIG. 19 schematically shows experimental procedures for amplifying DNA fragments that are microsatellite portions by PCR and gel electrophoresis. First, a pair of primer sequences 1900 and 1901 that sandwich a microsatellite of interest are designated and a genome region 1902 comprising the microsatellite and the primer sequences is amplified by PCR. FIG. 19 shows an example of a heterozygote, in which two homologous chromosomes differ in terms of the number of repeat units in a microsatellite. Since the homologous chromosomes differ in terms of the microsatellite length, two types of PCR amplification products of different lengths, namely DNA fragments (containing 52 nucleotides and 48 nucleotides, respectively), can be obtained. When these fragments are subjected to gel electrophoresis for a given period of time, the above two types of PCR amplification products are separated based on difference in DNA fragment length. Each DNA fragment is previously labeled with fluorescence dye, followed by electrophoresis. Then, the intensities and the positions of the fluorescence signals of the DNA fragments are detected. Thus, as shown in FIG. 19, a graph on which the DNA fragment length (fragment size) and the fluorescence signal intensity (i.e., abundance of DNA fragment) are plotted on the horizontal axis and the vertical axis, respectively, can be obtained. In addition, when PCR amplification products are subjected to electrophoresis simultaneously with DNA fragments with known lengths (size markers) so as to detect fluorescence signals, the length of each PCR amplification product can be obtained based on the position at which a size marker is detected.

Experimental techniques involving gel electrophoresis are described above. Also, such techniques can be carried out using capillary electrophoresis whereby the length of a DNA fragment is examined by allowing a sample to migrate through a thin tube filled with gel and measuring a period of time required for the sample to migrate a certain distance (normally to the end of a capillary). Upon capillary electrophoresis, it is usual to detect a sample using a fluorescence signal detector that is installed at the end of a capillary, instead of scanning a fluorescence signal from a sample in gel.

Noise Generated During PCR and Electrophoresis Experiments

The peak results shown in FIG. 19 can be obtained when PCR and electrophoresis are carried out in an ideal process. In an actual experiment, a variety of noise peaks are generated in many cases. Examples of major noise peaks upon interpretation of experimental results include stutter peaks and +A peaks.

As shown in FIG. 20, stutter peaks are generated by a phenomenon in which a complementary strand of a template sequence strand to be replicated is formed upon PCR at a position where a continuous repetitive sequence of a microsatellite has slipped, resulting in formation of a hairpin-loop template strand (slipped-strand mispairing). Thus, a DNA fragment to be replicated has a microsatellite with an increased or decreased number of repeat units so that a noise peak is observed based on a fluorescent signal from the DNA fragment having an allele with the increased or decreased number of repeat units. In particular, it has been known that such noise peak tends to be generated when microsatellites having short unit lengths are amplified. In addition to a peak derived from a DNA fragment having the same length as the original DNA fragment, stutter peaks derived from a DNA fragment having a length that has increased or decreased by the integer multiple of a unit length of a microsatellite is observed.

+A peaks are generated by a phenomenon in which an excess nucleotide (normally "A") is added to a DNA fragment due to a replicase action upon replication of a DNA fragment by PCR. Thus, a +A peak is observed as a noise peak based on a fluorescence signal from a DNA fragment length to which a single nucleotide has been added. Such addition of a single nucleotide occurs to each DNA fragment from which a stutter peak is generated as described above, as well as to an original DNA fragment subjected to replication. Thus, based on a fluorescence signal, a +A peak is observed to be located at a distance of 1 unit length to the right of each stutter peak.

FIG. 21 shows a schematic view of a situation in which stutter peaks and +A peaks as described above are observed. FIG. 21 shows a waveform of a heterozygote containing two alleles. The waveform contains two peaks, each of which corresponds to an allele size having the same length as an original DNA fragment subjected to replication (hereafter referred to as a "true peak"). In addition, the waveform consists of two sets of peaks in which a center peak is a true peak. A first set of peaks contains stutter peaks that are located at distances of 2 units to the left, 1 unit to the left, and 1 unit to the right of a true peak. The sets also contain +A peaks corresponding to the true peak and the stutter peaks. A second set of peaks contains stutter peaks that are located at distances of 1 unit to the left and 1 unit to the right of a true peak. The set also contains +A peaks corresponding to the true peak and the stutter peaks. Hereafter, a true peak or a stutter peak that corresponds to a DNA fragment to which a single nucleotide is not added and that is responsible for generation of a particular +A peak is referred to as an "original peak."

Non-Patent Document 1 and the like teaches methods for determining true peaks from a plurality of peaks comprising noise peaks in the waveform of a fluorescence signal from a given individual, such signal being obtained during PCR and electrophoresis experiments.

Also, some methods for evaluating genotyping results have been reported and disclosed in Patent Document 1, Non-Patent Document 1, and the like. In addition, the software "TrueAllele" from Cybergenetics and the software "GeneMapperID" from Applied Biosystems (ABI) have been known to have functions for evaluating genotyping results.

[Patent Document 1] JP Patent Publication (Kokai) No. 2006-17461 A

[Non-Patent Document 1] Matsumoto T. et al., "Novel algorithm for automated genotyping of microsatellites," Nucleic Acids Research, Vol. 32, No. 20 (2004) pp. 6069-6077

SUMMARY OF THE INVENTION

It has been desired that a technique of automated genotyping be combined with a technique for evaluating results of automated genotyping. This is because, in practice, when researchers interpret results of automated genotyping, genotyping accuracy obtained by evaluating such results is combined with the results of automated genotyping, and otherwise, it is impossible to judge whether or not visual inspection of results is required and whether or not results are valid.

In addition, Patent Document 1 teaches a method whereby true peaks of a group of individuals associated with the same marker are determined with the use of information obtained by calculating the characteristics and the pattern of appearance of stutter peaks and of +A peaks. However, there are concerns about deterioration in determination accuracy when a group with a sufficient number of individuals is not used in a single process. In a method whereby information obtained by calculating the characteristics and the pattern of appearance of stutter peaks and of +A peaks is used for a group of individuals associated with the same marker, specifically, a linear regression line of the height ratio of each original peak to each +A peak is calculated in a manner similar to that described in Non-Patent Document 1. In such method, such an original peak and a +A peak are each located at distance of the integer multiple of a unit length from a true peak on either side thereof in the waveform of each individual. Then, it is determined whether or not each peak contained in an observed waveform is a true peak, stutter peak, or +A peak based on the linear regression line. However, when the number of individuals to be used for calculation of a linear regression line is insufficient, fluctuation in the waveforms of some individuals has a large influence on the calculation. Thus, a linear regression line that represents a group of individuals cannot be calculated. Therefore, there are concerns that the inaccurate results of peak determination based on observed waveforms obtained using such linear regression line would be obtained. However, based on the fact that the number of groups of individuals used in a single process depends on the number of samples used in a single experiment, it is difficult to control the number of individuals to be used in a single process.

The present invention has been made under the above circumstances. It is an objective of the present invention to provide a method and a system for evaluating results of automated genotyping, comprising obtaining sufficient information regarding the characteristics of stutter peaks and of +A peaks from a particular marker even in a case with a small number of groups of individuals that can be used associated with such particular marker in a single process.

Based on considerations described below and with reference to the technical idea of the invention disclosed in Patent Document 1, the inventors of the present have conceived of the means for solving the above problems.

First, the inventors of the present invention focused on the following characteristics regarding the height ratio of a stutter peak to a +A peak of a particular marker and the fragment length of such marker.

Characteristic 1 The height ratio of a stutter peak to a true peak is reproducible.

The absolute value of the peak height of each stutter peak based on a fluorescence signal is not reproducible because it varies depending on experimental plates or experimental opportunities. However, when the same allele of the same marker is considered as described below, the height ratio of a stutter peak to a true peak is reproducible. The mechanism of generation of stutter peaks depends on a phenomenon related to a phenomenon of generation of true peaks from an allele. Thus, when a DNA fragment having the length of the same allele of the same marker is amplified, generation of stutter peaks takes place to such an extent that it is of relatively the same level as that at which generation of a true peak from the allele takes place. For instance, in FIG. 1, the waveform of the first individual is almost equivalent to the waveform of the second individual in terms of the height ratio of a stutter peak to a true peak (the height ratio of 101 to 100 and the height ratio of 103 to 102) when the stutter peak is located at a distance of 1 unit to the left of the true peak in the second set of peaks.

Characteristic 2 The height ratio of a +A peak to a true peak is reproducible when the same experimental protocol, in which duration of replicase action is included, is used.

Also, in the case of a +A peak, when the same marker is considered, the height ratio of a +A peak to a true peak is reproducible. As with the case of stutter peaks, generation of +A peaks takes place relative to generation of original peaks (true peaks or stutter peaks). Meanwhile, it has been known that the level of generation of +A peaks is strongly influenced by the length of duration of replicase action. In general, when a DNA fragment of the same allele of the same marker is amplified, an experimental protocol is fixed so that the duration for enzyme activation (duration before enzyme deactivation) is considered to be constant. Thus, also, +A peaks are expected to be reproducible.

For instance, in FIG. 1, the waveform of the first individual is almost equivalent to that of the second individual in terms of the height ratio of a +A peak to a true peak (the height ratio of 104 to 100, the height ratio of 106 to 105, the height ratio of 108 to 107, and the height ratio of 109 to 102) in the first and second sets of peaks.

Characteristic 3 The possible fragment length associated with a true peak, stutter peak, or +A peak is known in many cases.

When a particular marker is subjected to genotype determination, the possible allele type of the marker has been previously examined and is known in many cases. Thus, the possible fragment length associated with a stutter peak is obtained in a manner such that the integer multiple of a unit is added to or subtracted from the possible fragment length of such allele type (associated with a true peak). Also, the possible fragment length associated with a +A peak is obtained in a manner such that a single nucleotide is added to the fragment length associated with an original peak (true peak or stutter peak). For instance, when the fragment length associated with a true peak is 44 nucleotides in the case of a marker having a unit length of 2 bases, the possible fragment length associated with a stutter peak is calculated as follows: 44−2=2 nucleotides; or 44+2=46 nucleotides and so on. Also, the possible fragment length associated with a +A peak is calculated as follows: 42+1=43 nucleotides; 44+1=45 nucleotides; or 46+1=47 nucleotides and so on.

Thus, the inventors of the present invention focused on the above three characteristics so as to realize a method and system provided with functions below, wherein sufficient information regarding characteristics of a stutter peak and those of a +A peak derived from a particular marker is obtained even in a case with a small number of groups of individuals subjected to a single process. Hereafter, a user or an operator of the system of the present invention is called a "user." In addition, a technique used for genotype determination is a technique whereby the height ratio relative to a true peak or the height ratio of a stutter peak to a +A peak is used for calculating the tendency of a pattern of appearance of a stutter peak and that of a +A peak relative to a true peak.

Function 1-1: Extension of a Database Regarding the Height Ratio of a Stutter Peak to a True Peak When reproducibility of the height ratio of a stutter peak to a true peak is considered, waveform information for a group of individuals subjected to each process is added to a database. When a particular marker is repeatedly subjected to the relevant process, information regarding the height ratio indicating characteristics and the pattern of appearance of a stutter peak can be used as information based on a sufficient number of individuals that is statistically highly stable within a system. It should be noted that, in order to construct a database that stores statistically highly stable data, it is necessary to detect an outlier for the group of individuals used in a process and an outlier for all the data stored in the database so as to carry out filtering data to be additionally registered, instead of additionally registering all the height ratios of the group of individuals subjected to the process. Filtering processes are performed according to two types of verification.

The first filtering is used by verifying a variance value of all the height ratios of a group of individuals in each process. It is suggested that a user can define the threshold of a variance value of all the height ratios of a group of individuals in each process. With the use of such threshold, it is verified whether or not a variance value of the height ratios of the group of individuals is below or equal to the threshold. In the case of a variance value below or equal to the threshold, all the height ratios are additionally registered. In the case of a variance value exceeding the threshold, the result is displayed (step 603 in FIG. 6 described below) and none of the height ratios are additionally registered. (As described below, FIG. 14 shows an example of a display of a variance value of all the height ratios of a group of individuals exceeding the threshold.)

The second filtering is used by verifying the relationship between the mean value of the height ratios of each individual in a group of individuals in each process and the standard deviation of all the data. Herein the term "all data" indicates a combination of all the data stored in a database and all the data for a group of individuals subjected to a current process. Thus, the mean value and the standard deviation of height ratios of all the data are obtained (step 602 in FIG. 6 described below). The height ratios of the individual are additionally registered, only when the mean value of the height ratios of an observed waveform of each individual is within the range indicated by the following formula: (mean value of all data)+/−2*(standard deviation of all data). If one of the height ratios is not within such range, it is not additionally registered in a database.

As a result of the above two forms of filtering for verification, data determined to be appropriate are added to a database. With this function, it becomes possible to extend a database of height ratios with the use of appropriate determination results alone.

Herein, in order to determine in the filtering processes whether or not an outlier is obtained from an observed waveform, a 95% confidence interval based on the mean value and the standard deviation of all the height ratios is employed; however, selection of a standard value for determination and selection of statistics values are not limited thereto.

Function 1-2: Function of Detecting an Outlier of the Height Ratio of a Stutter Peak to a True Peak When the observed waveform is not determined to be appropriate during the first or second filtering in function 1-1, a warning indicating that an outlier has been obtained from the waveform is displayed with the two types of verification results. With this function, it becomes possible to confirm whether or not appropriate genotyping results are obtained from a group of individuals in each process.

Function 2-1: Function of Extending a Database Regarding the Height Ratio of a +A Peak to a True Peak When reproducibility of the height ratio of a +A peak to a true peak is considered, waveform information for a group of individuals subjected to each process is added to a database. When a particular marker is repeatedly subjected to the relevant process, information regarding the height ratio indicating characteristics and the pattern of a +A peak can be used as information based on a sufficient number of individuals that is statistically highly stable within a system. It should be noted that, in order to construct a database that stores statistically highly stable data, it is necessary to detect an outlier for the group of individuals used in a process and an outlier for all the data stored in the database so as to carry out filtering data to be additionally registered, instead of additionally registering all the height ratios of the group of individuals subjected to the process.

The first filtering is used to verify a variance value of all the height ratios of a group of individuals in each process. It is assumed that a user can define the threshold of a variance value of all the height ratios of a group of individuals in each process. With the use of such threshold, it is verified whether or not a variance value of the height ratios of the group of individuals is below or equal to the threshold. In the case of a variance value below or equal to the threshold, all the height ratios are additionally registered. In the case of a variance value exceeding the threshold, the result is displayed (step 703 in FIG. 7 described below) and none of the height ratios are additionally registered. (As described below, FIG. 15 shows an example of a display of a variance value of all the height ratios of a group of individuals exceeding the threshold.)

The second filtering is used by verifying the relationship between the mean value of the height ratios of each individual in a group of individuals in each process and the standard deviation of all the data. Herein the term "all data" indicates a combination of all the data stored in a database and all the data for a group of individuals subjected to a current process. Thus, the mean value and the standard deviation of height ratios of all the data are obtained (step 702 in FIG. 7 described below). The height ratios of the individual are additionally registered, only when the mean value of the height ratios of an observed waveform of each individual is within the range indicted by the following formula: (mean value of all data)+/− 2*(standard deviation of all data). If one of the height ratios is not within such range, it is not additionally registered in a database.

As a result of the above two forms of filtering for verification, data determined to be appropriate are added to a database. With this function, it becomes possible to extend a database of height ratios with the use of appropriate determination results alone.

Herein, in order to determine in the filtering processes whether or not an outlier is obtained from an observed waveform, a 95% confidence interval based on the mean value and the standard deviation of all the height ratios is employed; however, selection of a standard value for determination and selection of statistics values are not limited thereto.

Function 2-2: Function of Detecting an Outlier of the Height Ratio of a +A Peak to a True Peak When the observed waveform is not determined to be appropriate during the first or second filtering in function 2-1, a warning indicating that an outlier has been obtained from the waveform is displayed with the two types of verification results. With this function, it becomes possible to confirm whether or not appropriate genotyping results are obtained from a group of individuals in each process.

Function 3-1: Function of Extending a Database with the Addition of Information Concerning Fragment Length Values for a Group of Individuals in Each Process The possible fragment length associated with a true peak, stutter peak, or +A peak is known in many cases. Based on such fact, when peaks are detected in a group of individuals which are subjected to a process involving a particular marker, fragment length values are obtained based on the peaks so that appropriate values among the fragment length values are stored in a database. Thus, it is possible to verify whether or not a fragment length value associated with a peak that is detected from a particular individual in a given process is appropriate by examining whether or not such value is within the range of the fragment length value stored in a database, such value being associated with a peak that can be detected based on the same marker (step 806 in FIG. 8 described below).

Peak information regarding a particular individual (individual subjected to verification) obtained in each process is compared with peak information stored in a database that stores data regarding an allele, such data containing a larger number of records than the number of records that has previously been defined by a user.

First, true peaks are verified. When true peaks are identical to each other, stutter peaks and +A peaks on both sides of the true peaks are verified. A system displays a warning to a user when fragment length information associated with a particular stutter peak or +A peak is stored in a database but is not detected from an individual subjected to verification. It also displays a warning when such fragment length information is not stored in a database but is detected from an individual subjected to verification. In particular, when fragment length information associated with a particular stutter peak or +A peak is not stored in a database but is detected from an individual subjected to verification, the system displays a warning indicating that such fragment length information is not stored in a database. Further, as described in Characteristic 3, the system displays a warning and information concerning verification results obtained by comparing the unit length of a marker with the fragment length associated with a true peak and verifying whether or not the fragment length is a "possible" fragment length value associated with a peak by referring to the "determined reason for peak generation." Herein, the phrase "determined reason of peak generation"

indicates a finding that a stutter peak is generated at a fragment length value obtained in a manner such that the integer multiple of a unit length is added to or subtracted from the fragment length value associated with a true peak, and that a +A peak is generated based on a fragment length value obtained in a manner such that a single nucleotide is added to the fragment length value associated with an original peak (true peak or stutter peak).

As a result of the above verification, data determined to be appropriate are added to a database. With this function, it becomes possible to extend a database of fragment lengths with the use of appropriate determination results alone.

Function 3-2: Function of Detection of an Outlier Following Addition of Information Concerning Fragment Length Values for a Group of Individuals in Each Process When the observed waveform is not determined to be appropriate during the function 3-1, a warning indicating that an outlier has been obtained from the waveform is displayed with the verification results. With this function, it becomes possible to confirm whether or not appropriate genotyping results are obtained from a group of individuals in each process.

It is an objective of the present invention to provide the following system for evaluating genotyping results as a realized embodiment with the functions described above:

an evaluation system for displaying analysis results of the length of a PCR amplification product of a DNA fragment containing a microsatellite, comprising:

a graph display processing unit for displaying a graph of detection signals of the PCR amplification product, in which the axes denote detection signal intensity and fragment length, respectively;

a first determination processing unit for determining +A peaks derived from the detection signals of the PCR amplification product in which one adenine is added to a DNA fragment end and peaks excluding +A peaks based on the detection signals of the PCR amplification product;

a second determination processing unit for determining true peaks derived from the detection signals of the PCR amplification product of the DNA fragment and stutter peaks derived from the detection signals of the PCR amplification product in which a microsatellite repetitive sequence is increased or decreased by one unit or more based on the detection signals of the PCR amplification product;

a determination result display processing unit for displaying the results of the determination of +A peaks and peaks excluding +A peaks, the results of the determination of true peaks and stutter peaks, together with the graph; and a database that stores analysis results of the length of the PCR amplification product of the DNA fragment containing the microsatellite obtained from each of a plurality of individuals;

wherein determination results obtained in the first and second determination processing units are evaluated based on at least one of the following criteria:

(1) whether or not the height ratio of a true peak and a stutter peak subjected to determination differs significantly from the same ratios derived from a plurality of individuals stored in the database;

(2) whether or not the height ratio of a true peak to a +A peak subjected to determination differs significantly from the same ratios derived from a plurality of individuals stored in the database; and (3) whether or not fragment lengths associated with true peaks, stutter peaks, and +A peaks subjected to determination differ significantly from those obtained from a plurality of individuals stored in the database.

In the system for evaluating genotyping results of the present invention, the database stores the analysis results of each individual and experimental protocols for the analysis, and that data stored in the database is used as criteria upon evaluation of the determination results only when the data corresponds, to a given extent, to data subjected to determination in terms of experimental protocols.

In the system for evaluating genotyping results of the present invention, analysis results for the data subjected to determination are stored in the database when determination results are evaluated as appropriate upon evaluation of the determination results.

As described above, in accordance with the evaluation method and system for genotyping results of the present invention, when carrying out a process of differentiating true peaks and noise peaks such as stutter peaks and +A peaks based on a graph showing fluorescence analysis results for an amplification product, it is possible to obtain high-quality information regarding noise peak characteristics based on a sufficient amount of data obtained in past processes using the same allele of the same marker, even if an insufficient number of individuals are used in a single process. Further, at the same time, it is possible to obtain information regarding whether or not a group of individuals subjected to the process and genotyping results for the individuals are appropriate (whether or not the results are outliers). Thus, it becomes possible to carry out each process for genotyping of a group of individuals with high accuracy even in cases involving small numbers of individuals, without additional experiments or processing costs.

BRIEF DESCRIPTION OF THE DRAWINGS

FIG. 18 shows polymorphisms in terms of the number of repeat units in a microsatellite that differ among different homologous chromosomes and individuals.

DESCRIPTION OF THE PREFERRED EMBODIMENTS OF THE INVENTION

Figure 1:
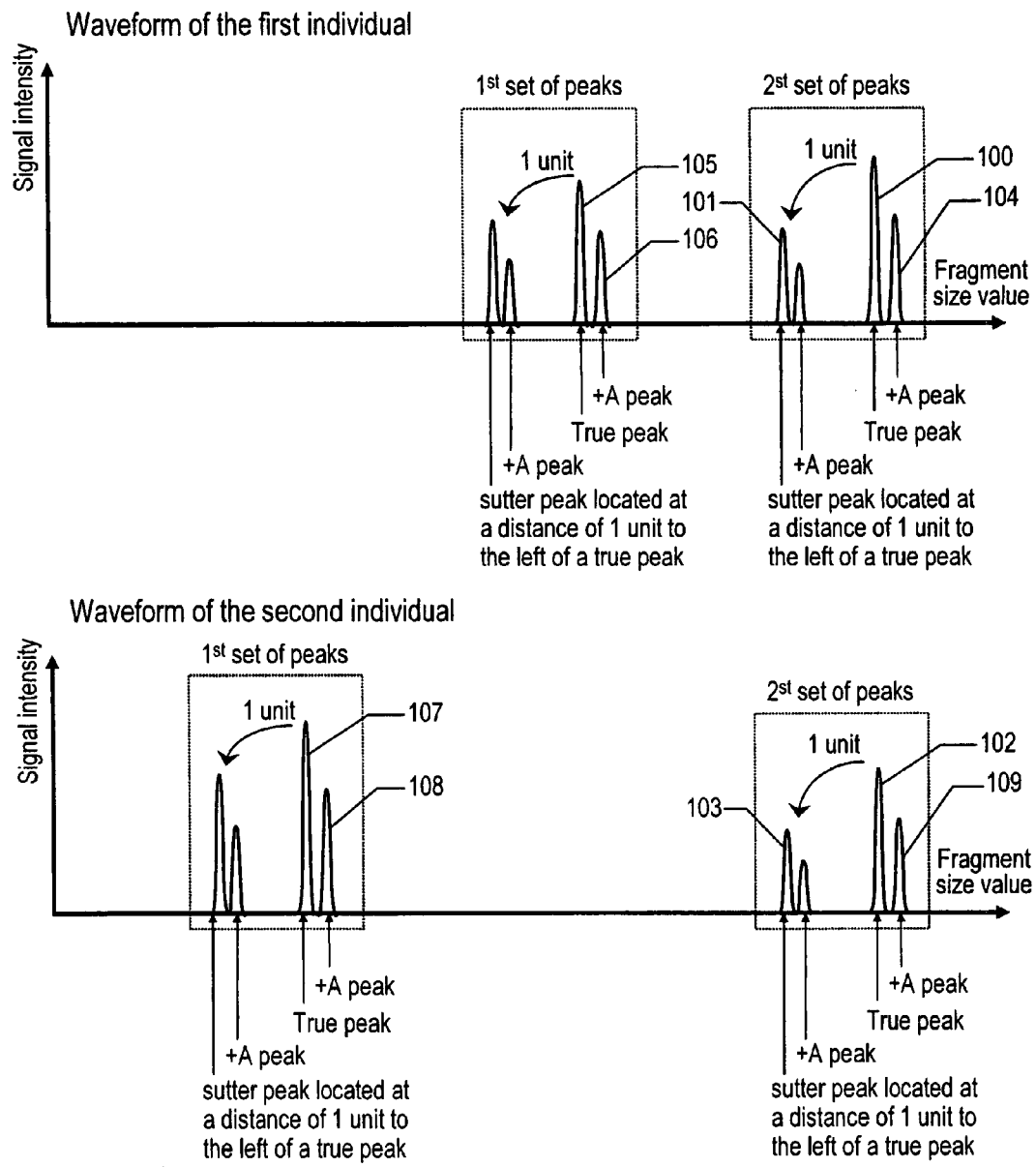
FIG. 1 shows that the height ratio of a stutter peak to a true peak and the height ratio of a +A peak to a true peak are reproducible.

Hereafter, the preferred embodiments for carrying out the method and system for evaluating genotyping results of the present invention will be described with reference to drawings. FIGS. 2 to 17 elaborate embodiments of the present invention. In the figures, identical reference numerals denote identical elements with basically identical structures and operations.

System Configuration

Figure 2:
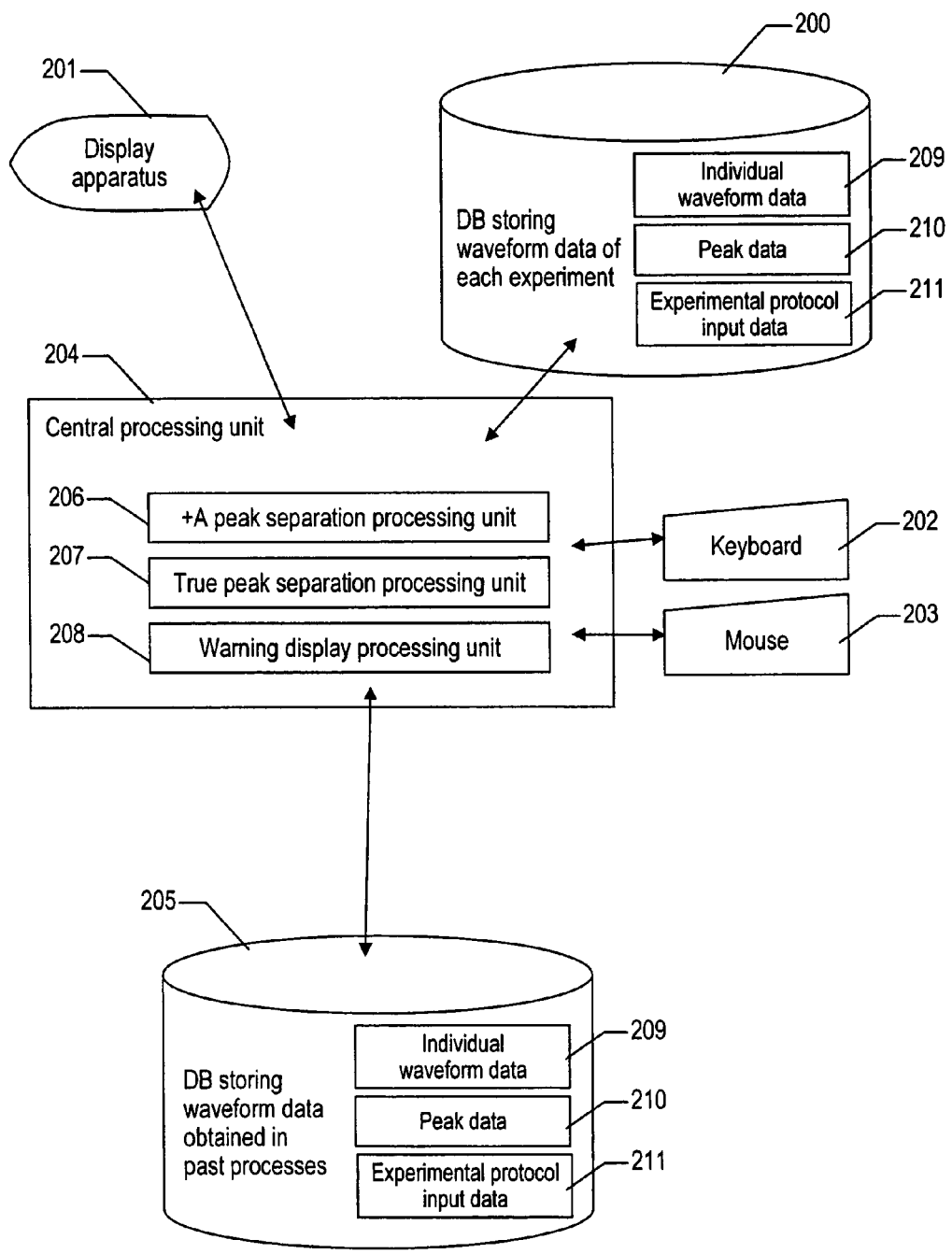
FIG. 2 schematically shows a functional block diagram of the internal configuration of a system for evaluating genotyping results, such system being constructed as one embodiment of the present invention.

FIG. 2 is a functional block diagram that schematically shows internal configuration of a system for evaluating genotyping results that is constructed as an embodiment of the present invention. The system for evaluating genotyping results comprises: a waveform data DB 200 that stores waveform data (waveform data for a group of individuals of interest) obtained by fluorescence analysis of PCR amplification products as a result of each PCR and electrophoresis; a display apparatus 201 that displays waveform data and related genotyping results; a keyboard 202 and a pointing device 203 such as a mouse that are used for carrying out the operation of selecting an individual or a peak that corresponds to the waveform data and the genotyping results displayed; a central processing unit 204 in which a necessary arithmetic process and a control process are carried out; and a DB 205 that stores the height ratios based on waveform data obtained in past processes.

A central processing unit 204 comprises: a +A peak separation processing unit 206 in which peaks that appear in waveform data are divided into a group of original peaks and a group of +A peaks during a genotyping process; a true peak separation processing unit 207 in which an original peak is determined to be a true peak or stutter peak during a genotyping process; and a warning display processing unit 208 that adds an individual that has been determined to be appropriate by the above function 1, 2, or 3 to a database and displays a result that an outlier with respect to all data has been obtained from a group of individuals or from an individual subjected to a process. A waveform data DB 200 and a DB 205 that stores the height ratios based on waveform data obtained in past processes each comprises: waveform data 209 associated with waveform data for each individual; peak data 210 obtained from waveform data for each individual; and experimental protocol input data 211.

Figure 3:
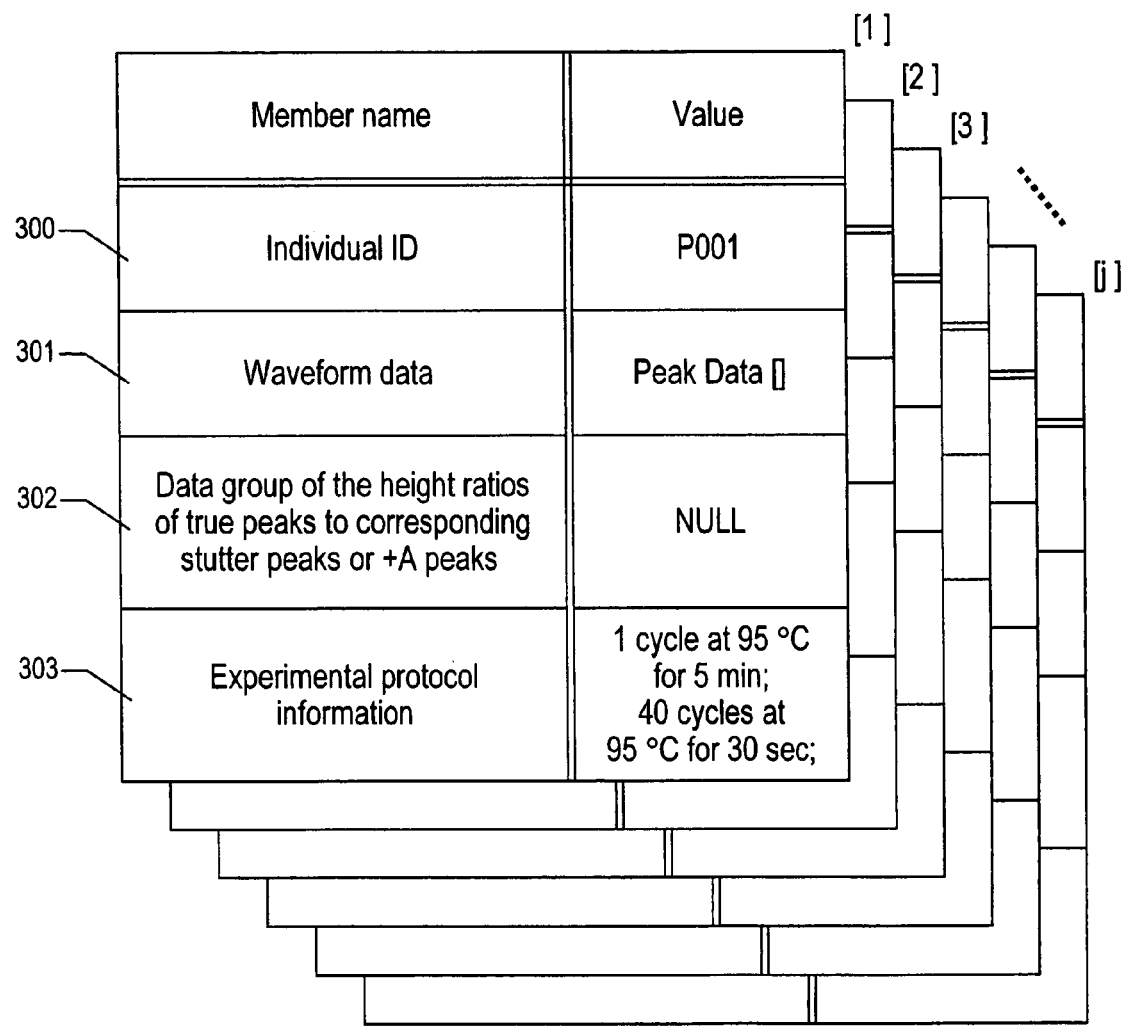
FIG. 3 shows a data structure of individual waveform data 209 contained in a waveform data DB 200 and a DB 205 that stores the height ratios from waveform data obtained in past processes in the genetic information display system shown in FIG. 2.

FIG. 3 shows a waveform data structure group for each individual, which is contained in a waveform data DB 200 and a DB 205 that stores the height ratios based on waveform data obtained in past processes. Such waveform data structure group "WaveFormData[ ]" comprises in terms of a number "j" of individuals in a group: an individual ID 300 for identification among individuals; waveform data 301 (corresponding to data shown in FIG. 4); data 302 of the ratio of a true peak to a corresponding +A peak; and experimental protocol information 303. Before waveform data is subjected to calculation, data 302 indicate NULL values.

Figure 4:
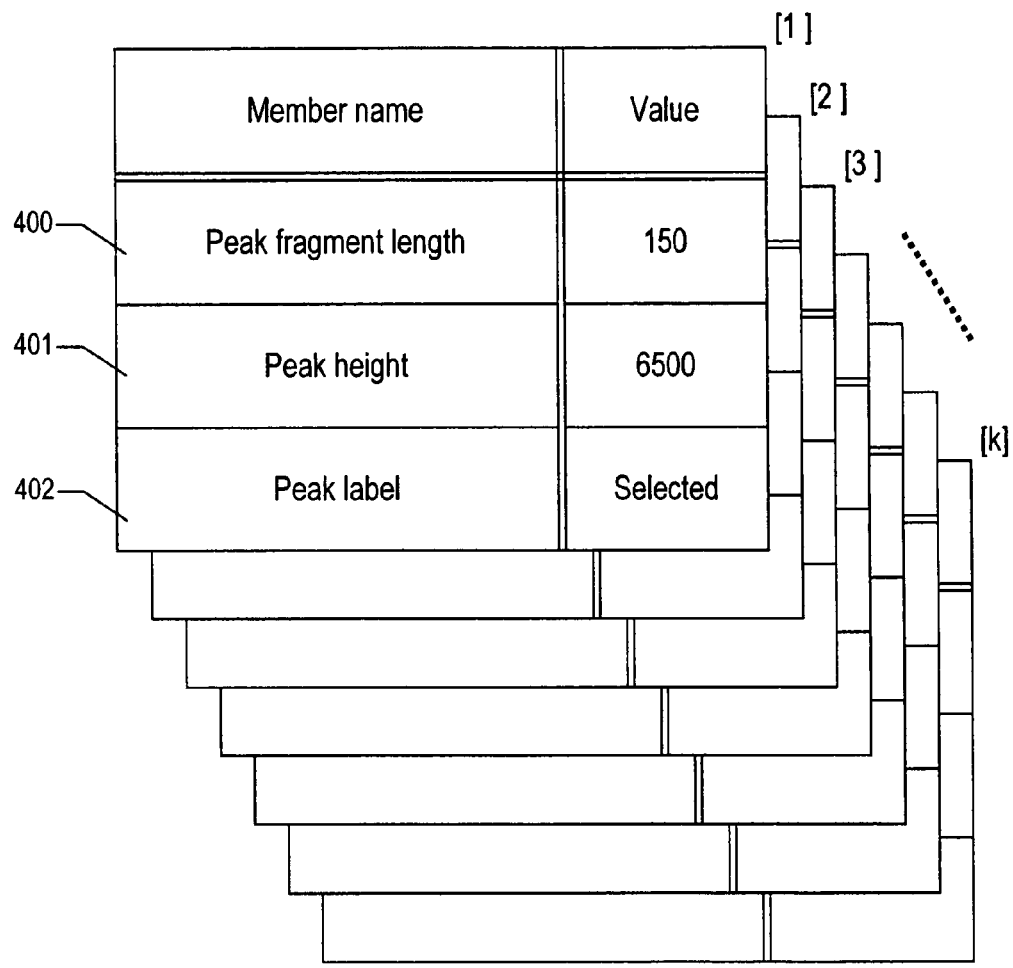
FIG. 4 shows a data structure of peak data 210 contained in a waveform data DB 200 and a DB 205 that stores the height ratios from waveform data obtained in past processes of the genetic information display system shown in FIG. 2.

FIG. 4 shows a peak data structure group based on waveform data contained in a waveform data DB 200 and a DB 205 that sores the height ratios based on waveform data obtained in past processes. Such peak data structure group "PeakData[ ]" comprises data regarding a number "k" of peaks. Such data includes a peak fragment length 400, a peak height 401, and a label 402 that indicates whether or not a peak is a true peak, a +A peak corresponding to a true peak, a stutter peak, or another +A peak. Data 402 stores one of the following indicators: "selected" for a true peak, "selected +A" for a +A peak corresponding to a true peak, "stutter" for a stutter peak that is not a true peak, and "+A" for a +A peak corresponding to a stutter peak that is not a true peak.

Operation Procedures for the System

Next, the flow of a process carried out under the system for evaluating genotyping results is described with reference to the flowcharts shown in FIGS. 5, 6, 7, and 8.

First, the system reads waveform data for each individual from a waveform data DB 200 (step 500). In this step, the system reads all individual waveform data associated with a microsatellite marker of interest that are stored in a waveform data DB 200 and the waveform data are kept as individual waveform data 209 and peak data 210 in a waveform data DB 200 and a DB 205 that stores the height ratios based on waveform data obtained in past processes. In addition, the system reads experimental protocol input data such that the data are kept as experimental protocol input data 211 in a waveform data DB 200 and a DB 205 that stores the height ratios based on waveform data obtained in past processes. Then, peaks of each individual are grouped into a group of +A peaks and a group of original peaks (step 501). This process is executed by a +A peak separation processing unit 206 of a central processing unit 204. Peak determination is carried out using conventional techniques. When a peak is determined to be a +A peak, a value indicating that the peak is a +A peak is recorded on a peak label 402 contained in peak data 210. Also, when a peak is determined to be an original peak, a value indicating that the peak is a true peak or stutter peak is recorded on a peak label 402 contained in peak data 210. In addition, the height ratio of an original peak to a +A peak for each group of peaks is recorded in data 302 contained in peak data 210. Further, experimental protocol input data are recorded in data 303.

Figure 9:
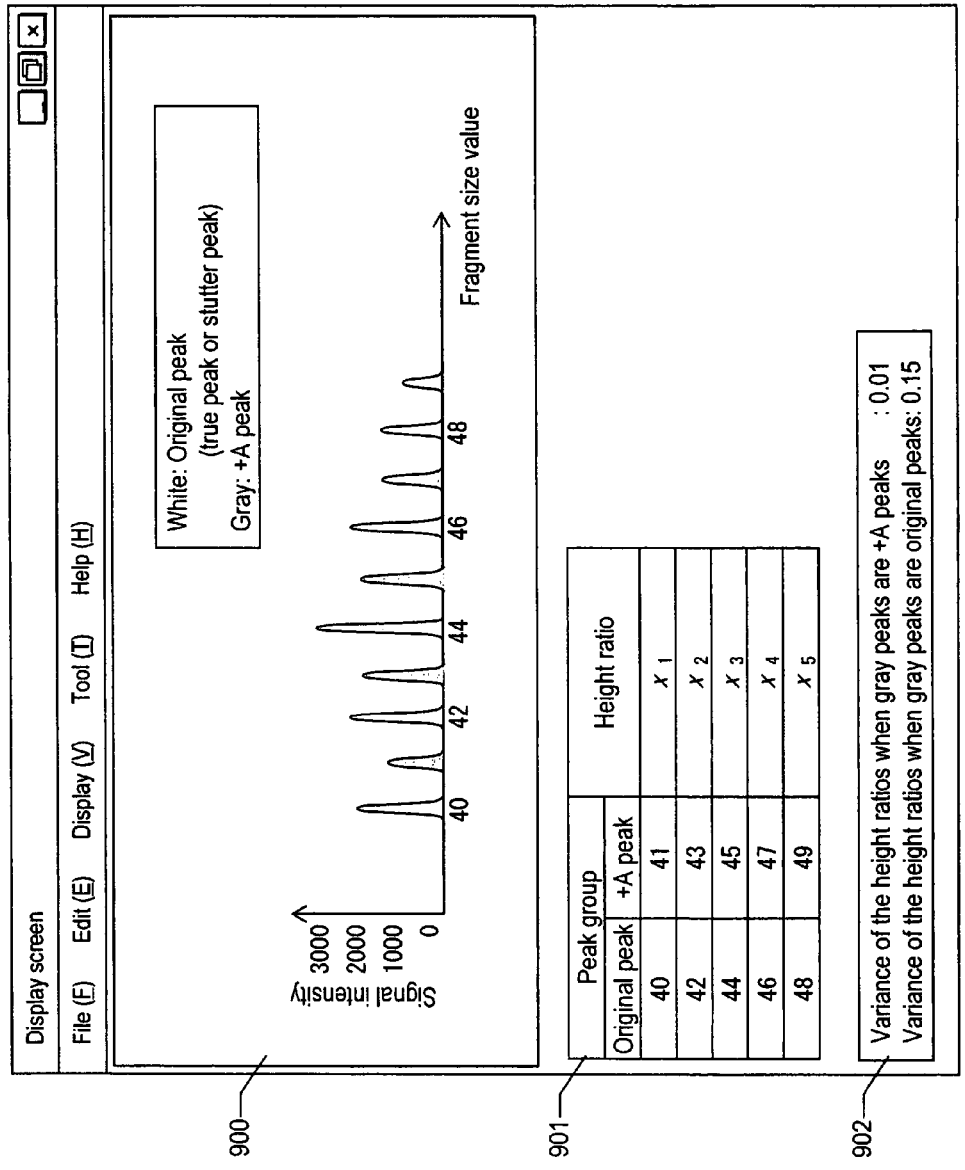
FIG. 9 shows a screen displaying a graph of results of a division of peaks of individual waveform data into a group of +A peaks and a group of original peaks in a +A peak separation processing unit.

As described above, peaks contained in waveform data for each individual are divided into a group of original peaks and a group of +A peaks such that the results are shown in a waveform as shown in FIG. 9 (step 502). A display screen shown in FIG. 9 displays: a result 900 obtained by dividing peaks of waveform data of a particular individual into a group of original peaks and a group of +A peaks; a table 901 that shows the fragment lengths and the height ratios of the respective groups of peaks; and a calculation result 902 indicating the variance value of the height ratios obtained by a method of dividing peaks into groups, wherein the highest peak is or is not determined to be as a +A peak.

Subsequently, each peak that has been determined to be a peak (original peak) other than a +A peak in step 501 is determined to be either a true peak or a stutter peak (step 503). This process is executed by a true peak separation processing unit 207 of a central processing unit 204. Peak determination is carried out using conventional techniques. The result for each peak is recorded on a peak label 402 of peak data 210. Further, in each individual case, the height ratio of a true peak to a +A peak is calculated. Then, the obtained height ratio is sequentially added as an element value of data 302 of individual waveform data 209.

Figure 10:
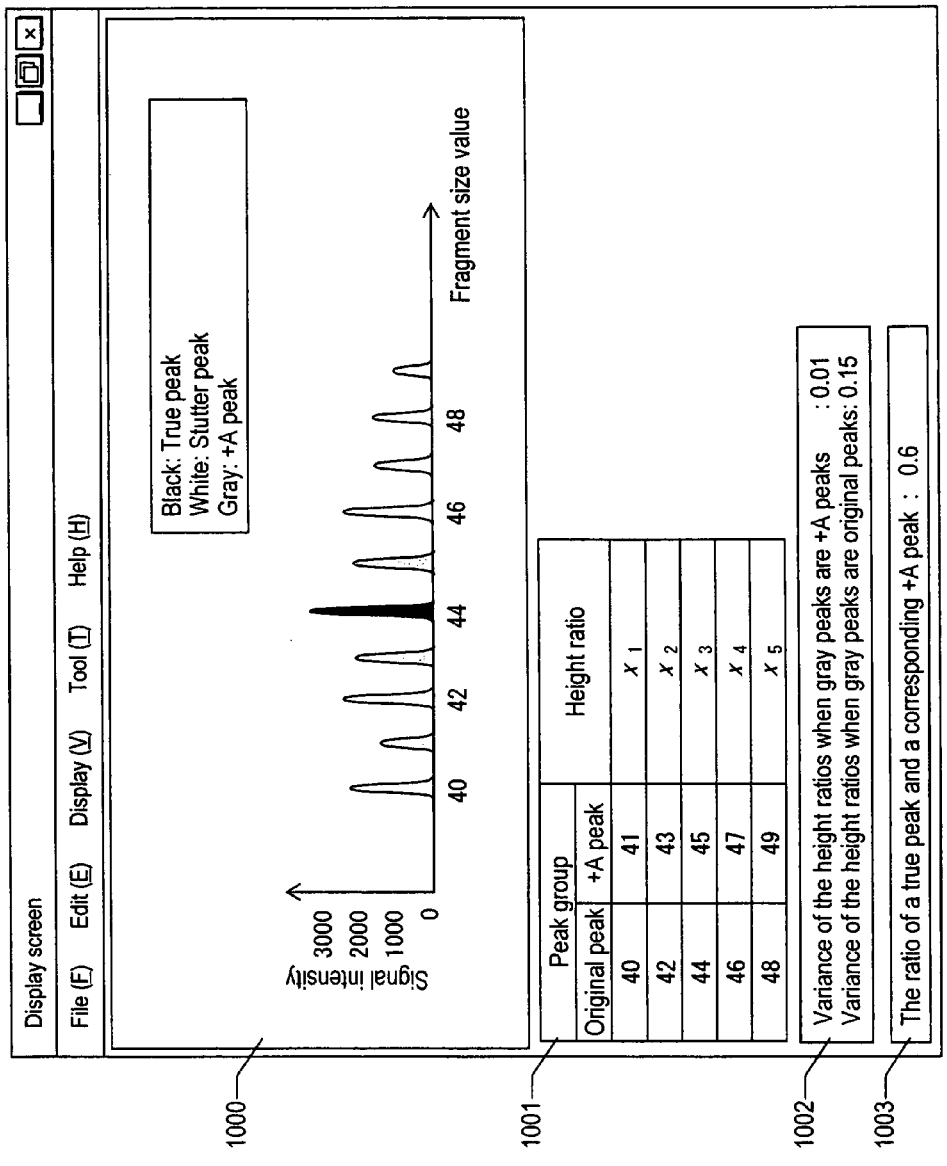
FIG. 10 shows a screen displaying a graph of results of a determination of original peaks contained in waveform data of each individual as true peaks or stutter peaks in a true peak separation processing unit.

As described above, peaks contained in waveform data for each individual are divided into a group of original peaks and a group of +A peaks such that the results are shown in a waveform as shown in FIG. 10. A display screen shown in FIG. 10 displays: a result 1000 obtained by dividing peaks of waveform data of a particular individual into a group of original peaks and a group of +A peaks; a table 1001 that shows the fragment lengths and the height ratios of the respective groups of peaks; and a calculation result 1002 indicating the variance value of the height ratios obtained by a method of dividing peaks into groups, wherein the highest peak is or is not determined to be as a +A peak.

Figure 6:
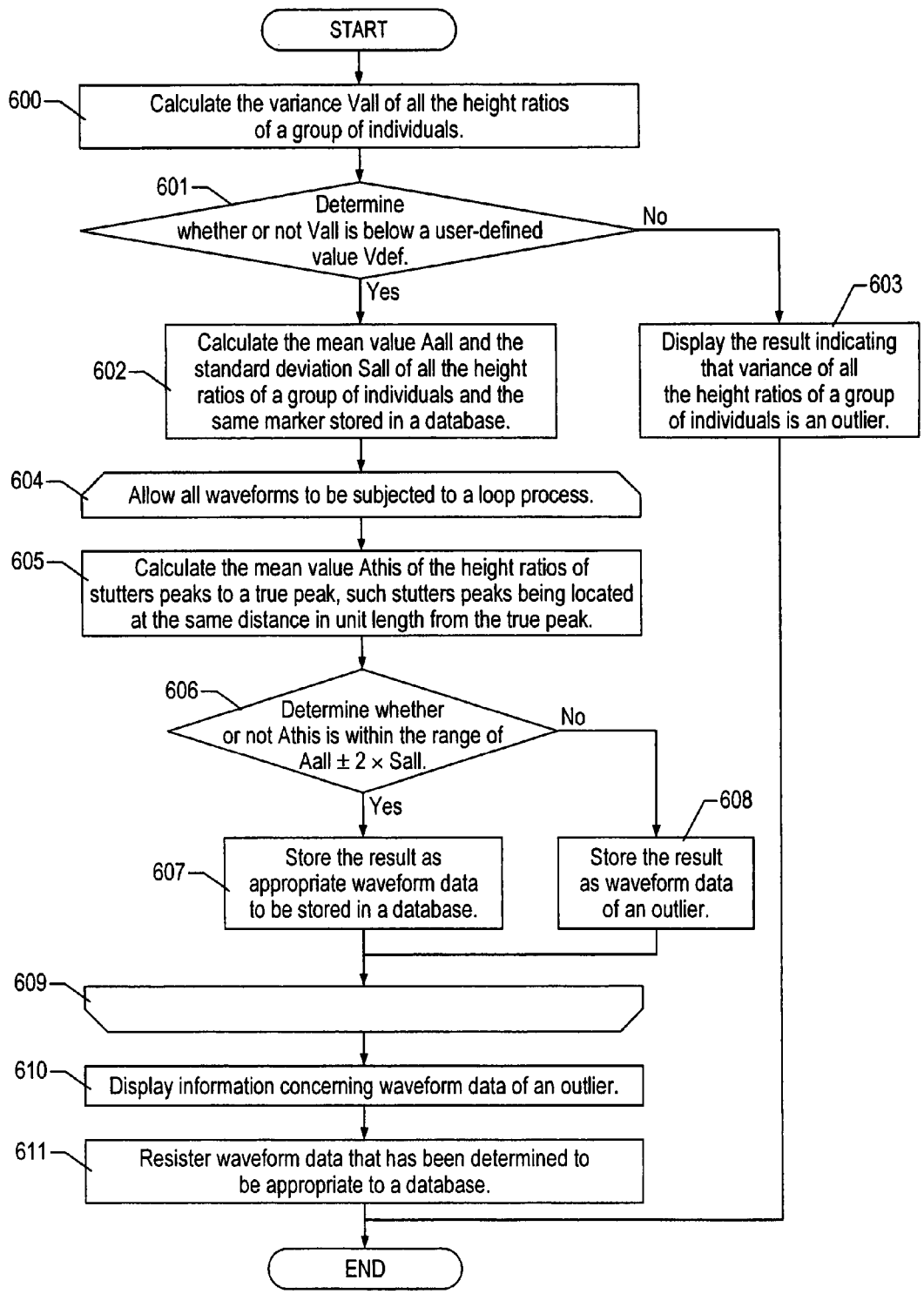
FIG. 6 shows a flowchart detailing a process of confirming the appropriateness of the height ratio of a true peak to each stutter peak in step 504 in FIG. 5.
Figure 11:
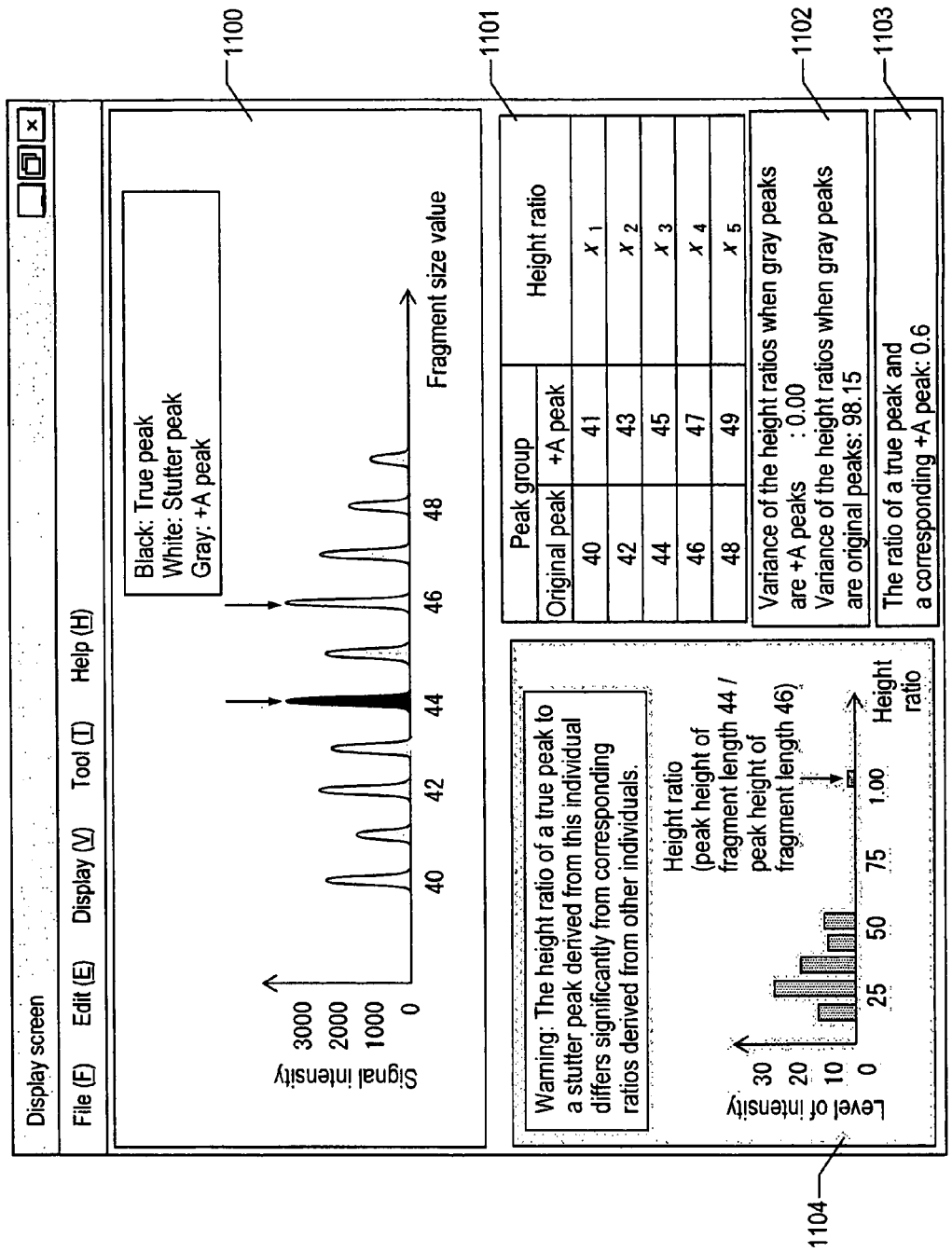
FIG. 11 shows a screen displaying a predetermined warning from a warning display processing unit when the height ratio of a true peak to a corresponding stutter peak deviates (is inappropriate) significantly from the corresponding value stored in a DB 205.

If the height ratio of a true peak to each stutter peak is determined to be significantly different (inappropriate) from a corresponding value stored in DB 205 as a result of a process of confirming whether or not the height ratio of a true peak and each stutter peak is appropriate in the subsequent step 504, (a process described below, which is shown in FIG. 6), a predetermined warning is displayed by a warning display processing unit 208 of a central processing unit 204 (a process in step 610 in FIG. 6). FIG. 11 shows an example of a warning display screen in such case. A warning display screen shown in FIG. 11 displays: a result 1100 obtained by determining each peak of waveform data for a particular individual as a +A peak, true peak, or stutter peak; table 1101 that shows the fragment lengths and the height ratios of the respective groups of peaks; a calculation result 1102 that indicates the variance value of the height ratios obtained by a method of dividing peaks into groups, wherein the highest peak is or is not determined to be as a +A peak; the height ratio of a true peak to a corresponding +A peak 1103; and a predetermined warning display 1104 with a histogram showing the height ratios of true peaks to corresponding stutter peaks in the cases of the individual of interest and other individuals.

Figure 7:
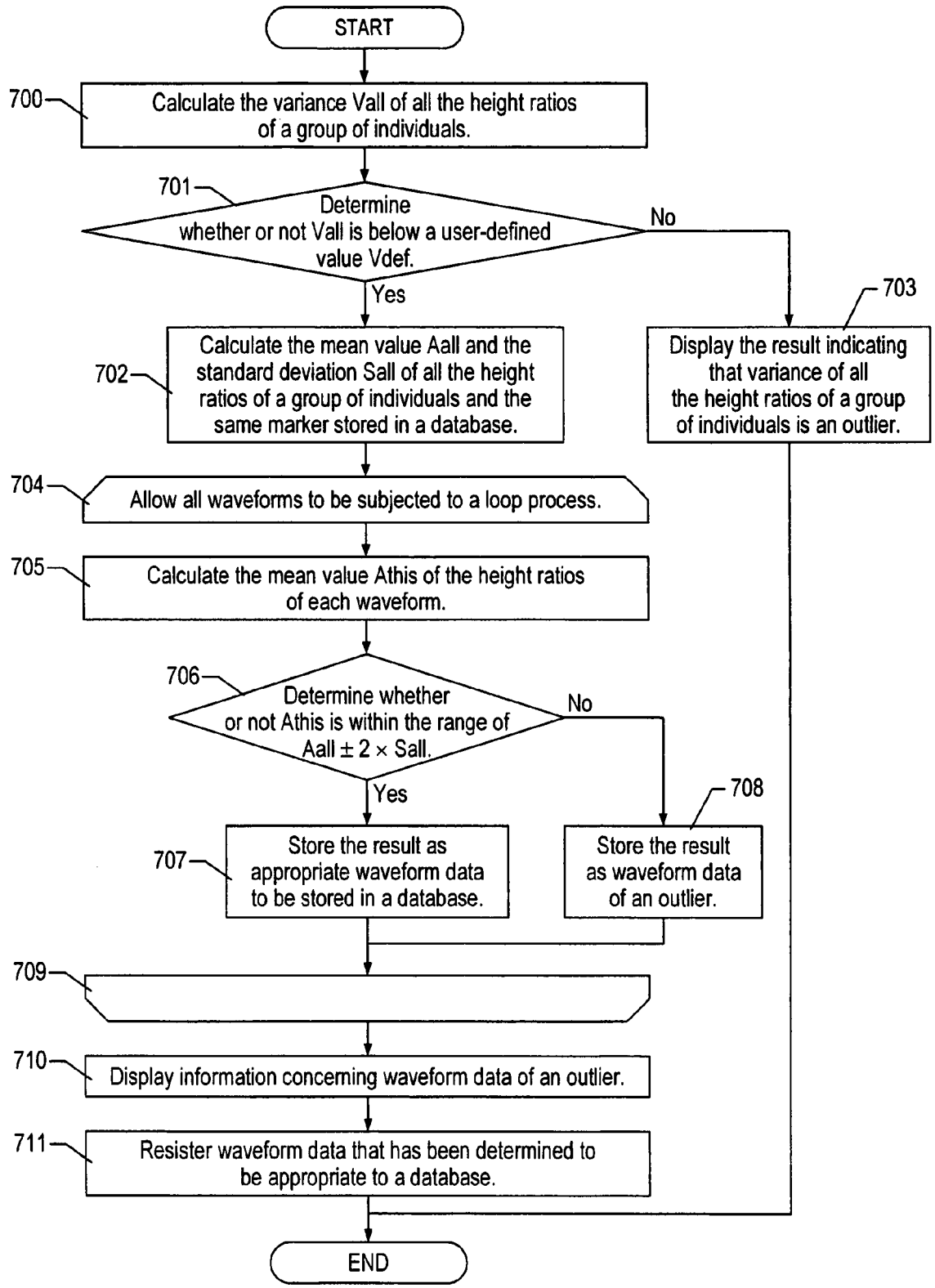
FIG. 7 shows a flowchart detailing a process of confirming the appropriateness of the height ratio of a true peak to each +A peak in step 505 in FIG. 5.
Figure 12:
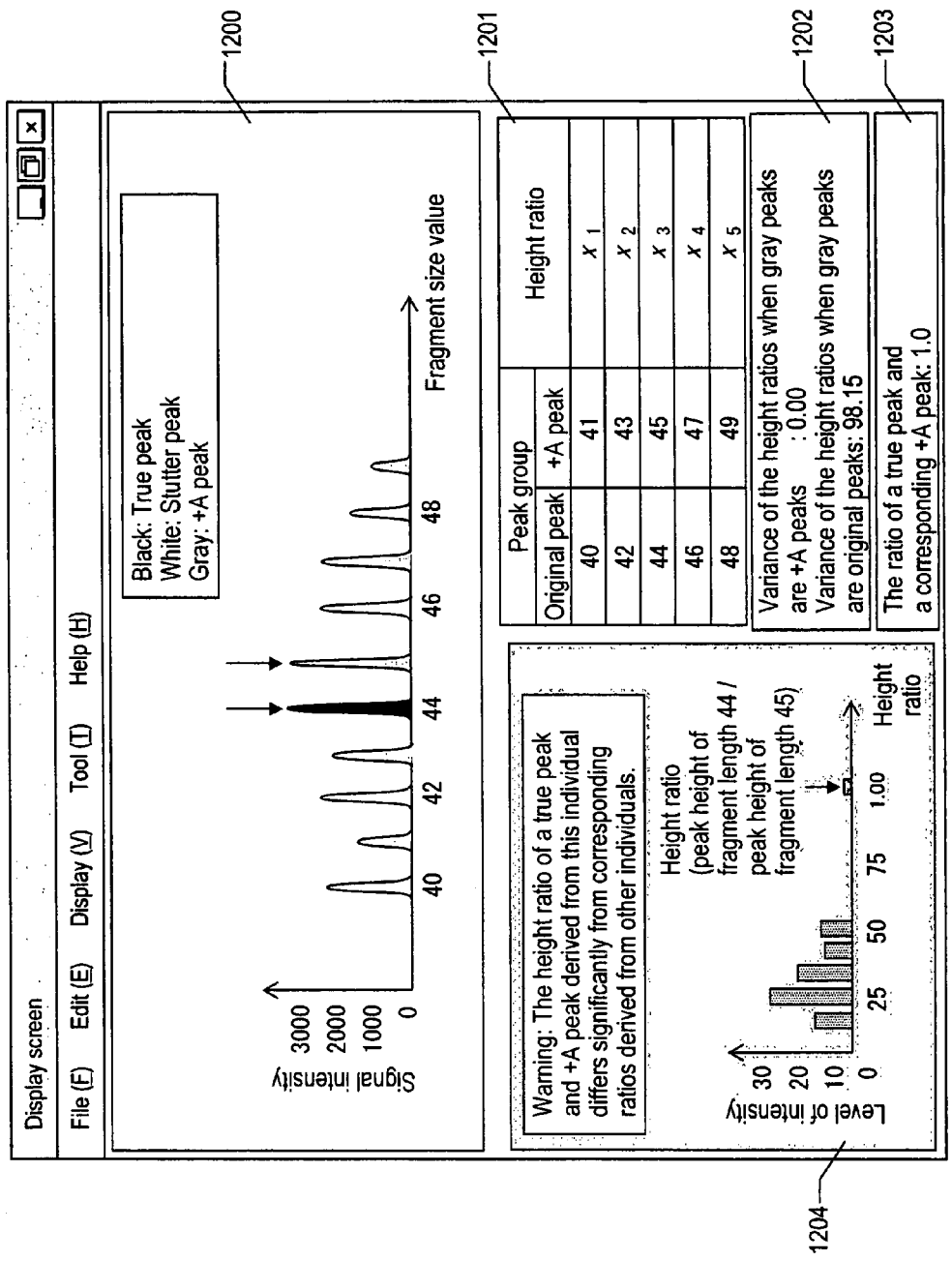
FIG. 12 shows a screen displaying a predetermined warning from a warning display processing unit when the height ratio of a true peak to a corresponding +A peak deviates (is inappropriate) significantly from the corresponding value stored in DB 205.

If the height ratio of a true peak to each +A peak is determined to be significantly different (inappropriate) from a corresponding value stored in DB 205 as a result of a process of confirming whether or not the height ratio of a true peak and each +A peak is appropriate in the subsequent step 505, (a process described below, which is shown in FIG. 7), a predetermined warning is displayed by a warning display processing unit 208 of a central processing unit 204 (a process in step 710 in FIG. 7). FIG. 12 shows an example of a warning display screen in such case. A warning display screen shown in FIG. 12 displays: a result 1200 obtained by determining each peak of waveform data for a particular individual as a +A peak, true peak, or stutter peak; table 1201 that shows the fragment lengths and the height ratios of the respective groups of peaks; a calculation result 1202 that indicates the variance value of the height ratios obtained by a method of dividing peaks into groups, wherein the highest peak is or is not determined to be as a +A peak; the height ratio of a true peak to a corresponding +A peak 1203; and a predetermined warning display 1204 with a histogram showing the height ratios of true peaks to corresponding +A peaks in the cases of the individual of interest and other individuals.

Figure 8:
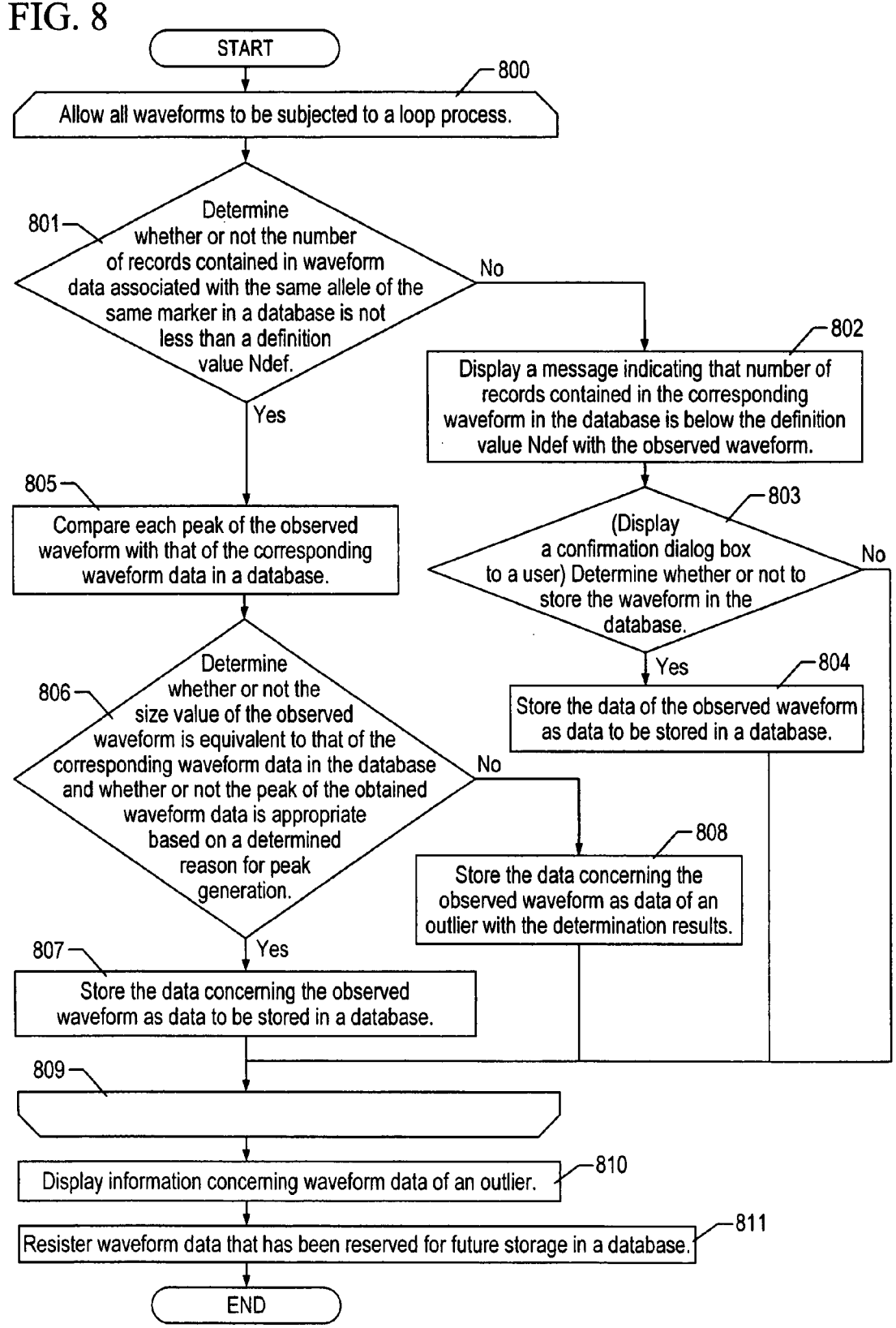
FIG. 8 shows a flowchart detailing a process of confirming the appropriateness of the fragment length value in step 506 in FIG. 5.
Figure 13:
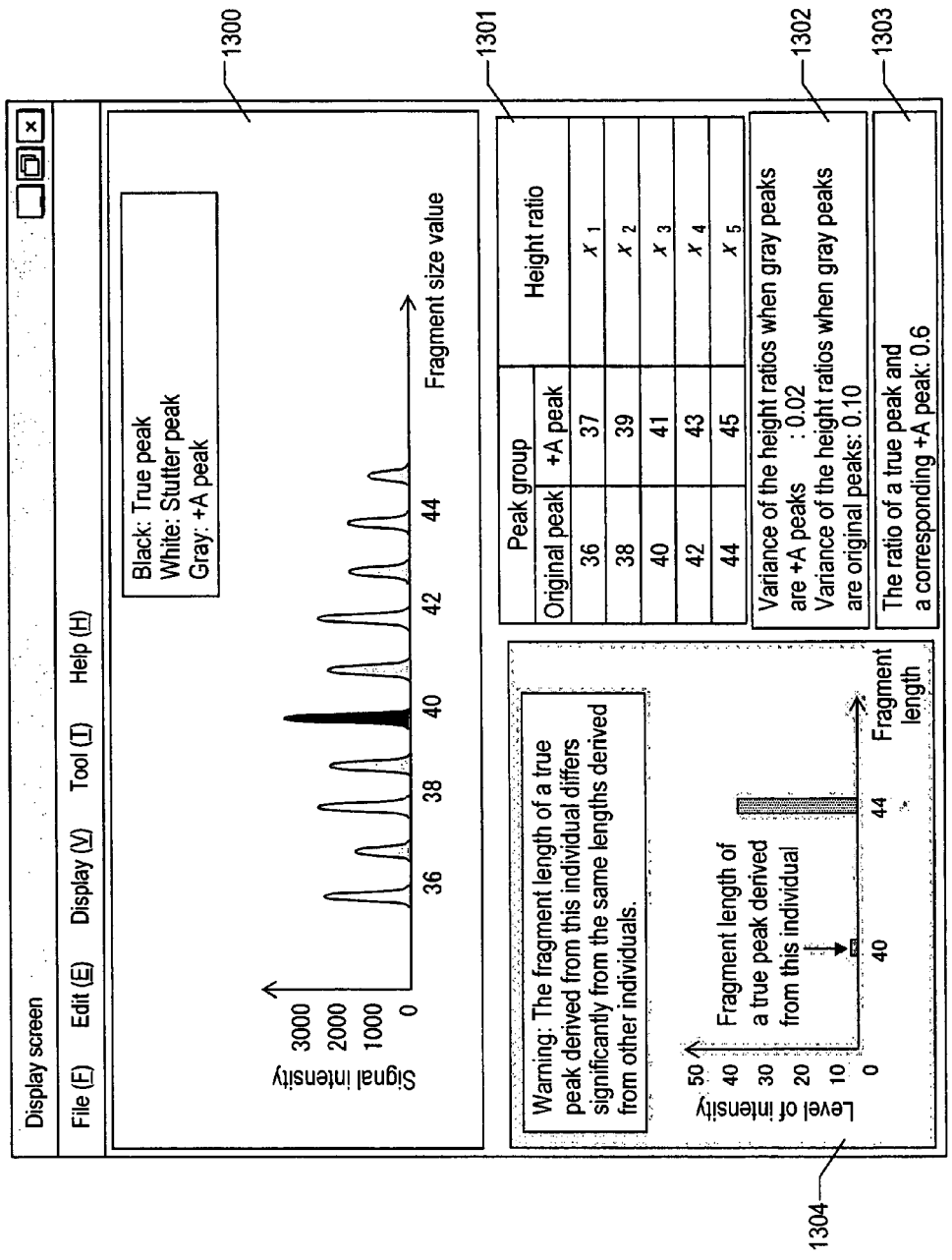
FIG. 13 shows a screen displaying a predetermined warning from a warning display processing unit when a fragment length value of an original peak or +A peak deviates significantly from the corresponding value stored in DB 205 (the value is inappropriate).

If the fragment length values of an original peak and a +A peak are determined to be significantly different (inappropriate) from corresponding values stored in DB 205 as a result of a process of confirming whether or not the fragment values of an original peak and a +A are appropriate in the last step 506, (a process described below, which is shown in FIG. 8), a predetermined warning is displayed by a warning display processing unit 208 of a central processing unit 204 (a process in step 810 in FIG. 8). FIG. 13 shows an example of a warning display screen in such case. A warning display screen shown in FIG. 13 displays: a result 1300 obtained by determining each peak of waveform data for a particular individual as a +A peak, true peak, or stutter peak; table 1301 that shows the fragment lengths and the height ratios of the respective groups of peaks; a calculation result 1302 that indicates the variance value of the height ratios obtained by a method of dividing peaks into groups, wherein the highest peak is or is not determined to be as a +A peak; the height ratio of a true peak to a corresponding +A peak 1303; and a predetermined warning display 1304 with a histogram showing the fragment lengths of true peaks to corresponding stutter peaks in the cases of the individual of interest and other individuals.

Figure 5:
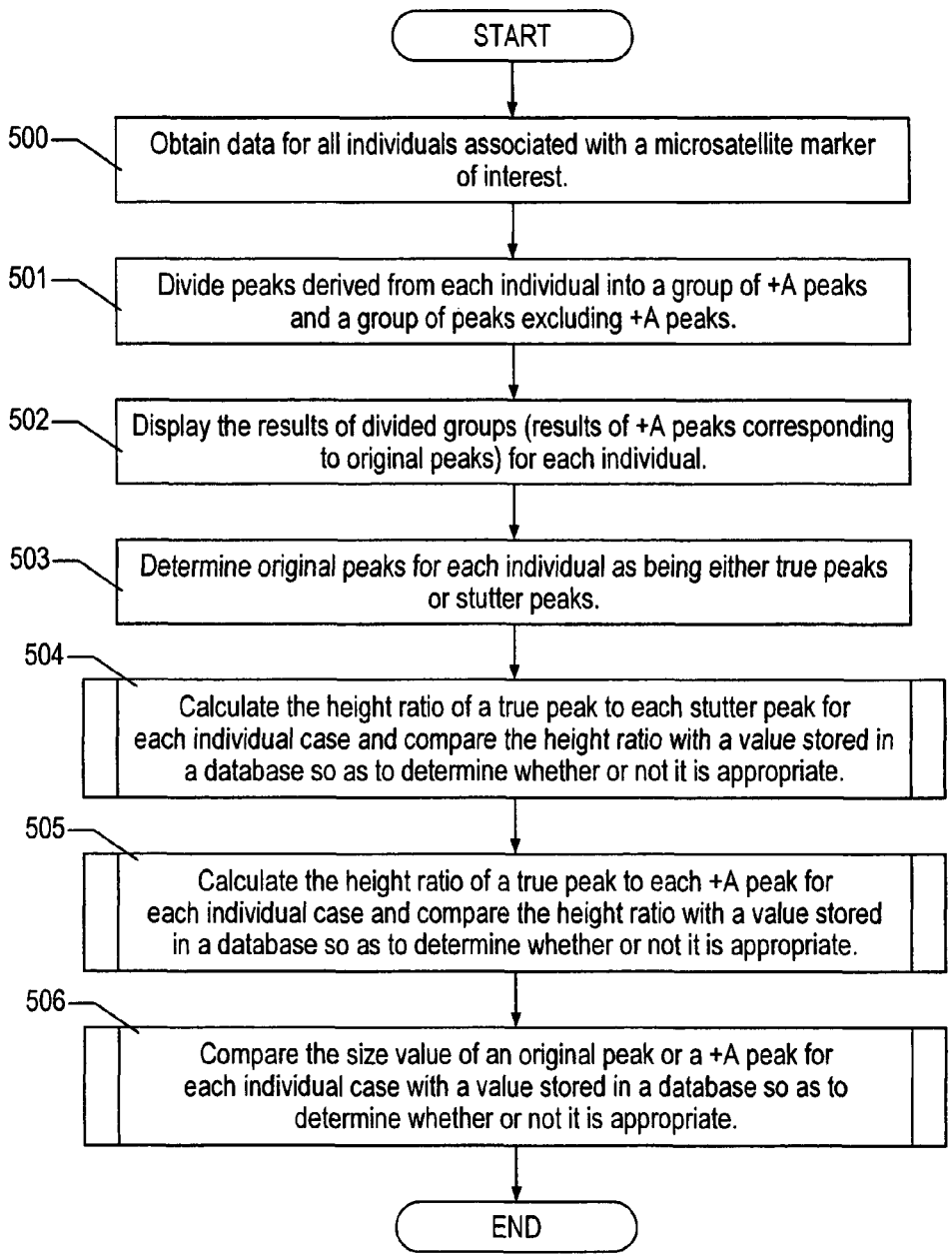
FIG. 5 shows a flowchart indicating the flow of a process carried out in the system for evaluating genotyping results shown in FIG. 2.
Figure 14:
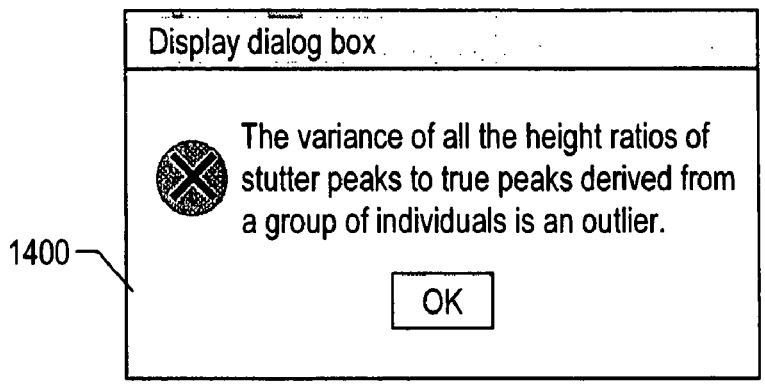
FIG. 14 shows an example of a dialog box indicating that a variance value of all the height ratios of true peaks to stutter peaks derived from a group of individuals is an outlier.

FIG. 6 shows a flowchart illustrating the details of the process of confirming appropriateness of the height ratio of a true peak to each corresponding stutter peak in step 504 of FIG. 5. This flowchart shows a process to which all individuals are subjected. First, the variance Vall of all the height ratios derived from all individuals is calculated (step 600). Then, it is determined whether or not the variance Vall of all the height ratios is below the value Vdef that is defined by a user (step 601). If the determination result of step 601 is "No," the variance value of all the height ratios of the group of individuals is displayed as an outlier (step 603). FIG. 14 shows an example of a dialog box displayed in step 603. The dialog box consists of a warning message and an "OK" button (1400). If the determination result of step 601 is "Yes," the mean value Aall and the standard deviation Sall are calculated based on all the height ratios that are derived from the group of individuals and that are stored in a DB 205 (step 602).

Subsequently, all individuals are subjected to a loop process described below (a process that loops between step 604 and step 609). First, the mean value Athis of the height ratios obtained from a waveform of each individual is calculated (step 605). Then, it is determined whether or not Athis is within Aall±2×Sall with respect to the Aall and the Sall that have been calculated in step 602 (step 606). If the determination result is "No," the individual waveform data are stored as waveform data of an outlier (step 608). If the determination result is "Yes," the individual waveform data are stored as appropriate waveform data to be additionally registered in a DB 205 (step 607). The aforementioned loop process is carried out until all individuals have been subjected to the process. Thus, a group of waveform data of an outlier and a group of appropriate waveform data to be additionally registered in DB 205 are separately stored. At the end, information regarding waveform data of an outlier is displayed (step 610) and a group of waveform data that have been determined to be appropriate is additionally registered in DB 205 (step 611). A screen displayed in step 610 is shown in FIG. 11 as described in step 504. This process corresponds to function 1-2. In addition, step 611 corresponds to function 1-1.

Herein, in order to determine whether or not an outlier is obtained from an observed waveform, a 95% confidence interval based on the mean value and the standard deviation of all the height ratios is employed; however, selection of a standard value for determination and selection of statistics values are not limited thereto.

Figure 15:
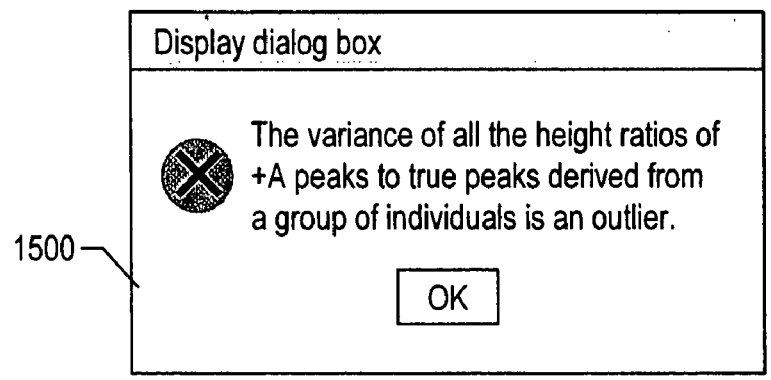
FIG. 15 shows an example of a dialog box indicating that a variance value of all the height ratios of true peaks to +A peaks derived from a group of individuals is an outlier.

FIG. 7 shows a flowchart illustrating the details of the process of confirming appropriateness of the height ratio of a true peak to each corresponding +A peak in step 505 of FIG. 5. This flowchart shows a process to which all individuals are subjected. First, the variance Vail of all the height ratios derived from all individuals is calculated (step 700). Then, it is determined whether or not the variance Vail of all the height ratios is below or equal to the value Vdef that is defined by a user (step 701). If the determination result of step 701 is "No," the variance value of all the height ratios of the group of individuals is displayed as an outlier (step 703). FIG. 15 shows an example of a dialog box displayed in step 703. The dialog box consists of a warning message and an "OK" button (1500). If the determination result of step 601 is "Yes," the mean value Aall and the standard deviation Sall are calculated based on all the height ratios that are derived from the group of individuals and that are stored in a DB 205 (step 702).

Subsequently, all individuals are subjected to a loop process described below (a process that loops between step 704 and step 709). First, the mean value Athis of the height ratios obtained from a waveform of each individual is calculated (step 705). Then, it is determined whether or not Athis is within Aall±2×Sall with respect to the Aall and the Sall that have been calculated in step 702 (step 706). If the determination result is "No," the individual waveform data are stored as waveform data of an outlier (step 708). If the determination result is "Yes," the individual waveform data are stored as appropriate waveform data to be additionally registered in a DB 205 (step 707). The aforementioned loop process is carried out until all individuals have been subjected to the process. Thus, a group of waveform data of an outlier and a group of appropriate waveform data to be additionally registered in DB 205 are separately stored. At the end, information regarding waveform data of an outlier is displayed (step 710) and a group of waveform data that have been determined to be appropriate is additionally registered in DB 205 (step 711). A screen displayed in step 710 is shown in FIG. 11 as described in step 505. This process corresponds to function 2-2. In addition, step 711 corresponds to function 2-1.

Figure 16:
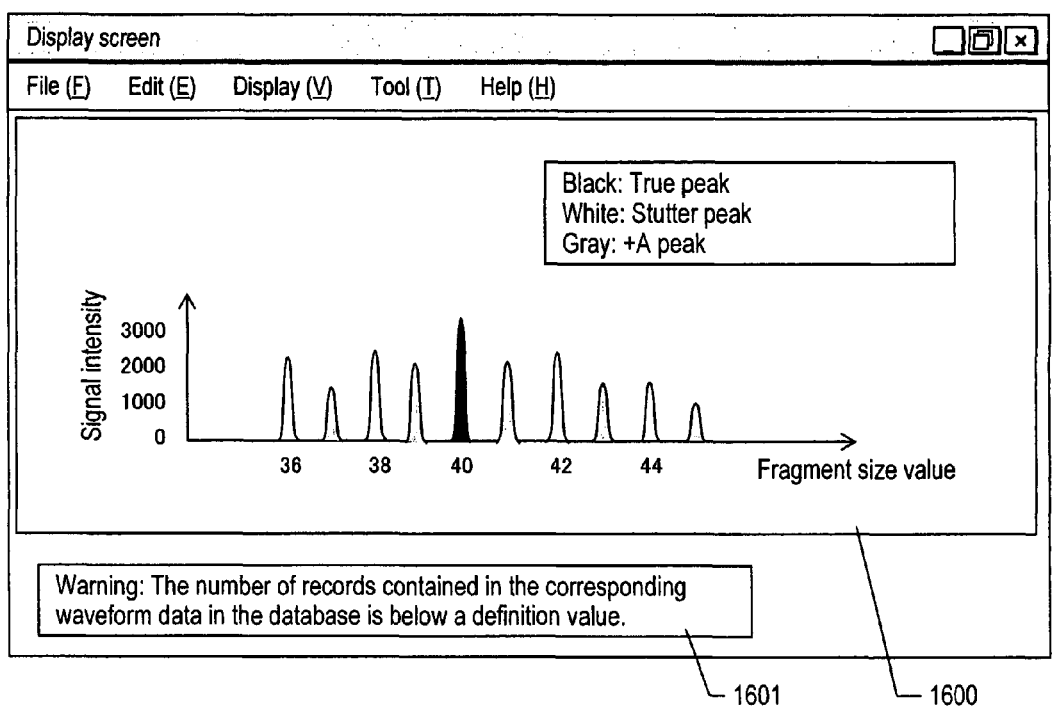
FIG. 16 shows an example of a screen indicating that the number of records contained in waveform data in a database that corresponds to an observed waveform is below a user-defined value.
Figure 17:
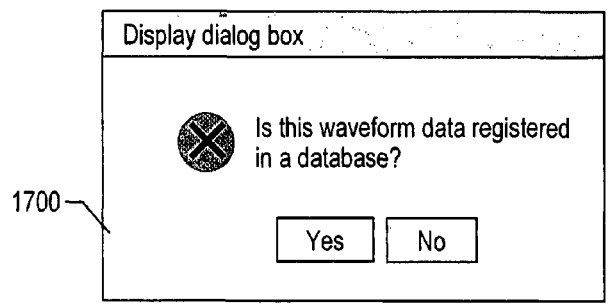
FIG. 17 shows an example of a dialog box for confirming whether or not to register observed waveform data in a database when the number of records contained in waveform data in a database that corresponds to an observed waveform is below a user-defined value.
Figure 19:
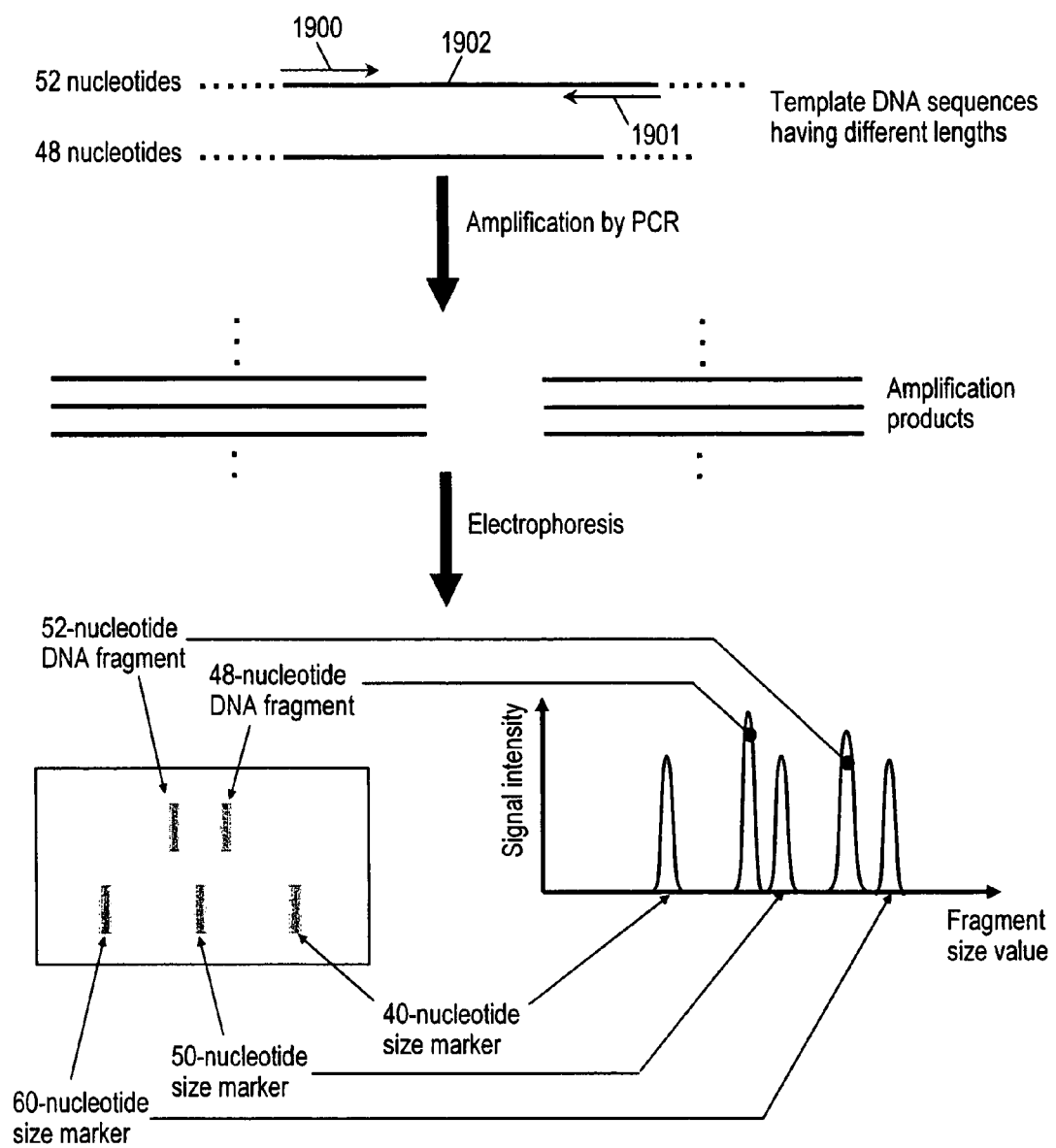
FIG. 19 shows typical experimental procedures for extraction and amplification of DNA fragments that are microsatellite portions by PCR and electrophoresis.
Figure 20:
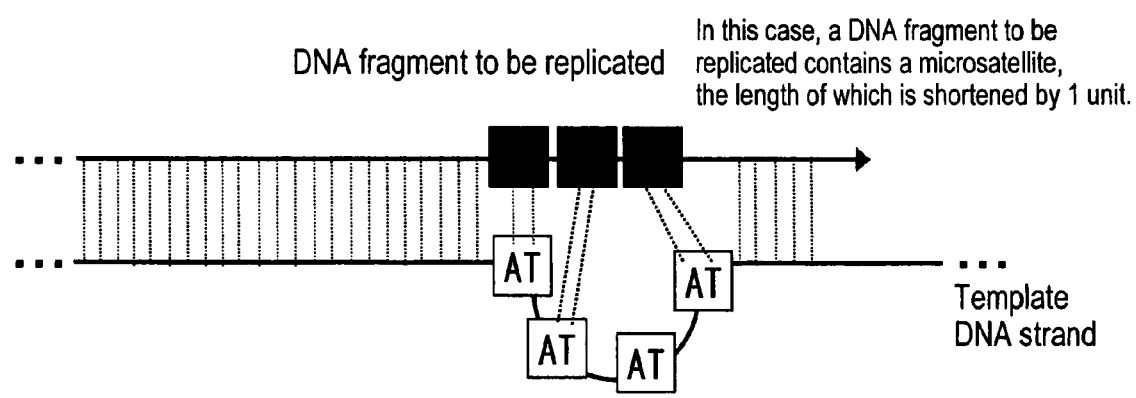
FIG. 20 shows a slippage phenomenon during PCR that causes generation of stutter peaks.
Figure 21:
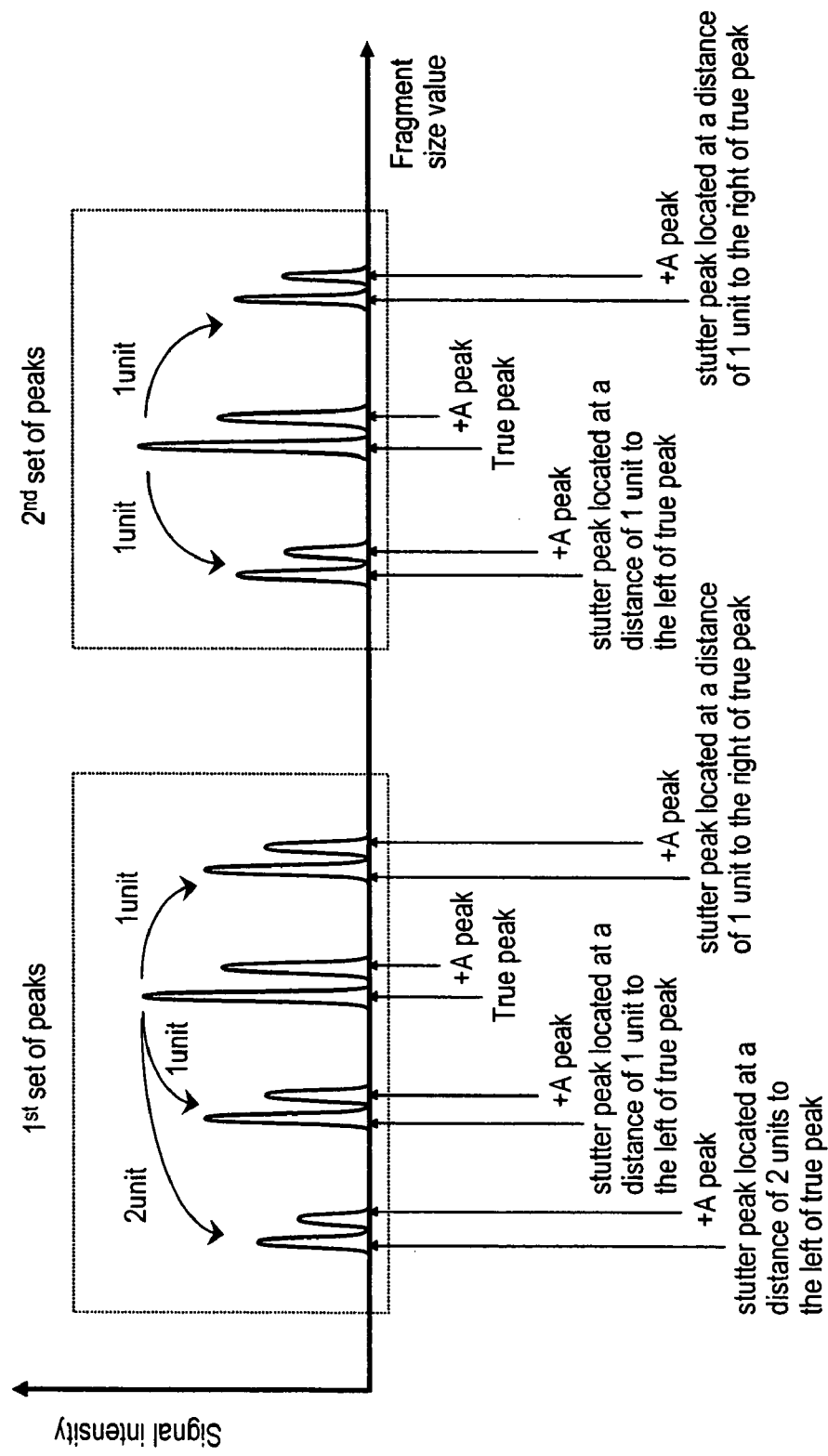
FIG. 21 shows a general waveform having true peaks, stutter peaks that are each located at a distance of 1 unit length to the left or right of the corresponding true peak, and +A peaks that are each located at a distance of one nucleotide to the right of the corresponding true peak or stutter peak. In addition, this figure shows an example in which an individual waveform having 2 sets of peaks each including a true peak is observed.

FIG. 8 shows a flowchart illustrating the details of the process of confirming appropriateness of the fragment length value of an original peak or a +A peak in step 506 of FIG. 5. This flowchart shows a process to which all individuals are subjected. The process described below is carried out in a loop (a process that loops between step 800 and step 809). First, it is determined whether or not the number of records contained in the corresponding waveform data (the number of records contained in fragment length value data) associated with the same allele of the same marker that has been registered in a DB 205 is not less than a user-defined value Ndef (step 801). If the determination result of step 801 is "No," a message indicating that the number of records contained in the corresponding waveform data that has been registered in DB 205 is below the user-defined value Ndef is displayed with an observed waveform (step 802). FIG. 16 shows an example of a display screen of step 802. The screen comprises waveform data display unit 1600 and warning message display unit 1601. Simultaneously, a confirmation dialog box is displayed with a message asking the user to decide whether or not to additionally add observed waveform data to DB 205 (step 803). FIG. 17 shows an example of the confirmation dialog box displayed in step 802. This confirmation dialog box comprises a confirmation message, a "Yes" button, and a "No" button (1700). When a user selects additional registration (Yes) with the confirmation dialog box displayed in step 803, the observed waveform is stored as waveform data to be stored in a database (step 804).

Meanwhile, if the determination result in step 801 is "Yes," each peak of the observed waveform data is compared with each peak of the corresponding waveform data that has been registered in DB 205 (step 805). Then, it is determined whether or not the observed waveform data corresponds to the waveform data that has been registered in DB 205 in terms of the fragment length value of each peak. At such time, a peak that is found only in the observed waveform data or the registered waveform data may exist. Thus, as described in function 3-1, with reference to a determined reason for peak generation, such peak is determined based on the appropriateness of the peak depending on the type of the peak, such as stutter peak or +A peak (step 806). If the determination result is "No," the observed waveform data is stored as waveform data of an outlier with information regarding the determination result (step 808). If the determination result is "Yes," the observed waveform data is stored as waveform data to be additionally added to DB 205 (step 807). The aforementioned loop process is carried out until all individuals have been subjected to the process. Thus, a waveform data group of an outlier and a waveform data group that is appropriate to be additionally added to DB 205 are separately stored. At the end, information about waveform data of an outlier is displayed (step 810) and a waveform data group that has been determined to be appropriate is additionally registered in DB 205 (step 811). Step 810 corresponds to function 3-2. Also, step 811 corresponds to function 3-1.

As above, specific embodiments of the method and system for evaluating genotyping results of the present invention are described. The scope of the present invention is never restrained by descriptions given in the specification. Those skilled in the art can make numerous changes and modifications to the embodiments of the invention without departing from the spirit of the invention.

The system for evaluating genotyping results of the present invention can be implemented on a personal computer used as an experimental data analysis system, for example, together with a system for determining a genotype based on the height ratio of a peak to a true peak, the height ratio of a stutter peak to a +A peak, and tendency of a pattern of appearance of a stutter peak or +A peak with respect to a true peak.

What is claimed is:

1. A system for evaluating results of the length of a PCR amplification product of a DNA fragment containing a microsatellite, said system comprising:

a processor for:
  (i) determining +A peaks derived from one or more detection signals of a PCR amplification product in which one adenine is added to the DNA fragment end and peaks excluding +A peaks based on the detection signals of the PCR amplification product; and
  (ii) determining true peaks derived from the detection signals of the PCR amplification product of the DNA fragment and stutter peaks derived from the detection signals of the PCR amplification product in which a microsatellite repetitive sequence is increased or decreased by one unit or more based on the detection signals of the PCR amplification product;

a display for displaying (i) a graph of a detection signals of a PCR amplification product, in which the axes denote detection signal intensity and fragment length, respectively; and (ii) the results of the determination of +A peaks and peaks excluding +A peaks, the results of the determination of true peaks and stutter peaks, together with the graph; and a storage device comprising a database of prior analysis results of the length of the PCR amplification product of the DNA fragment containing the same microsatellite obtained from each of a plurality of individuals, wherein said processor determines +A peaks and true peaks, respectively, based on at least one of the following criteria:

(1) whether or not the height ratio of a true peak and a stutter peak subjected to determination differs by more than a predetermined value from ratios derived from a plurality of individuals stored in the database;

(2) whether or not the height ratio of a true peak and a +A peak subjected to determination differs by more than a predetermined value from ratios derived from a plurality of individuals stored in the database; and (3) whether or not fragment lengths associated with true peaks, stutter peaks, and +A peaks subjected to determination differ by more than a predetermined value from those obtained from a plurality of individuals stored in the database.

2. The system according to claim 1, wherein the database further stores experimental protocols for the analysis together with the analysis results of each individual, and data stored in the database is used as criteria by the processor in evaluation of the detection signals when determining peaks only when the data was collected using the same experimental protocol as that used in producing the PCR application product.

3. The system according to claim 1, wherein analysis results generated by the processor when determining peaks are stored in the database when the results are analyzed and determined to be appropriate for inclusion in the database based on predetermined criteria.

4. The system according to claim 2, wherein analysis results generated by the processor when determining peaks are stored in the database when the results are analyzed and determined to be appropriate for inclusion in the database based on predetermined criteria.

* * * * *

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence:Synthetic
    DNA

<400> SEQUENCE: 1
gcttatatat ctgagtaat                                                19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:Synthetic
    DNA

<400> SEQUENCE: 2
gcttatatat atatctgag                                                19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:Synthetic
    DNA

<400> SEQUENCE: 3
gcttatatat atatatctg                                                19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:Synthetic
    DNA

<400> SEQUENCE: 4
gcttatatat atctgagta                                                19